US011174279B2

(12) United States Patent
Inoue et al.

(10) Patent No.: US 11,174,279 B2
(45) Date of Patent: Nov. 16, 2021

(54) METHOD FOR SYNTHESIZING RIBONUCLEIC ACID H-PHOSPHONATE MONOMER, AND OLIGONUCLEOTIDE SYNTHESIS IN WHICH SAID MONOMER IS USED

(71) Applicants: GeneDesign, Inc., Osaka (JP); NATIONAL INSTITUTE OF ADVANCED INDUSTRIAL SCIENCE AND TECHNOLOGY, Tokyo (JP)

(72) Inventors: Satoshi Inoue, Osaka (JP); Kohei Himeno, Osaka (JP); Hirokazu Nankai, Osaka (JP); Mutsuo Tanaka, Ibaraki (JP); Teiichi Murakami, Ibaraki (JP)

(73) Assignees: NATIONAL INSTITUTE OF ADVANCED INDUSTRIAL SCIENCE AND TECHNOLOGY, Tokyo (JP); GeneDesign, Inc., Osaka (JP)

( * ) Notice: Subject to any disclaimer, the term of this patent is extended or adjusted under 35 U.S.C. 154(b) by 241 days.

(21) Appl. No.: 16/310,938

(22) PCT Filed: Jun. 20, 2017

(86) PCT No.: PCT/JP2017/022691
§ 371 (c)(1),
(2) Date: Dec. 18, 2018

(87) PCT Pub. No.: WO2017/221929
PCT Pub. Date: Dec. 28, 2017

(65) Prior Publication Data
US 2020/0331945 A1 Oct. 22, 2020

(30) Foreign Application Priority Data
Jun. 21, 2016 (JP) .............................. JP2016-122554

(51) Int. Cl.
*C07H 1/02* (2006.01)
*C07H 19/067* (2006.01)
*C07H 19/167* (2006.01)

(52) U.S. Cl.
CPC ............ *C07H 1/02* (2013.01); *C07H 19/067* (2013.01); *C07H 19/167* (2013.01)

(58) Field of Classification Search
None
See application file for complete search history.

(56) References Cited

U.S. PATENT DOCUMENTS

| 2004/0023901 A1 | 2/2004 | Cook et al. |
| 2010/0152128 A1 | 6/2010 | Attenni et al. |
| 2012/0178710 A1* | 7/2012 | Jones ................... C07H 19/213 514/48 |
| 2012/0269903 A1 | 10/2012 | Montero et al. |
| 2019/0169223 A1* | 6/2019 | Sugawara ............. C07H 21/04 |

FOREIGN PATENT DOCUMENTS

| JP | 2005-524662 A | 8/2005 |
| JP | 2010-514768 A | 5/2010 |
| JP | 2010-527957 A | 8/2010 |
| JP | 2013-527128 A | 6/2013 |
| WO | WO-2006/063717 A2 | 6/2006 |
| WO | WO-2008/082601 A2 | 7/2008 |
| WO | WO-2008/082602 A2 | 7/2008 |
| WO | WO-2011/003025 A1 | 1/2011 |
| WO | WO-2011/028218 A1 | 3/2011 |
| WO | WO-2011/133871 A2 | 10/2011 |
| WO | WO-2012/017434 A2 | 2/2012 |
| WO | WO-2013/019874 A1 | 2/2013 |

OTHER PUBLICATIONS

Rozners et al., Nucleosides and Nucleotides, vol. 14, No. 3-5, pp. 855-857, 1995. (Year: 1995).*
European Patent Application No. 17815397.9, Extended European Search Report, dated Jan. 7, 2020.
Janesko et al., P(-O)H to P-OH Tautomerism: A Theoretical and Experimental Study, J. Org. Chem., 80(20):10025-32 (Oct. 2015).
Rozners et al., Evaluation of 2'-hydroxyl protection in RNA-synthesis using the H-phosphonate approach, Nucleic Acids Res., 22(1):94-9 (Jan. 1994).
Rozners et al., Synthesis of Oligoribonucleotides by the H-Phosphonate Approach Using Base Labile 2'-O-Protecting Groups. V. Recent Progress in Development of the Method, Nucleosides and Nucleotides, 11(9):1579-93 (Jan. 1992).
Greene et al. (eds.), Protective Groups in Organic Synthesis, Second Edition, New York, NY: John Wiley & Sons, Inc. (1991).
International Application No. PCT/JP2017/022691, International Search Report, dated Aug. 22, 2017.

(Continued)

*Primary Examiner* — Traviss C McIntosh, III
(74) *Attorney, Agent, or Firm* — Marshall, Gerstein & Borun LLP

(57) ABSTRACT

The present invention pertains to a method for synthesizing a ribonucleic acid H-phosphonate monomer, and a method for performing oligonucleotide synthesis in which said monomer is used. The present invention pertains to a method for manufacturing an inexpensively manufacturable H-phosphonate nucleoside derivative in which selective protection is provided to position 2' of a ribonucleoside monomer required in RNA oligonucleotide synthesis. The present invention is characterized in that: hydroxyl groups in position 2' and position 3', which have slightly different reactivity, are caused to react with an aromatic acyl halide at low temperature to selectively esterify position 2'; and subsequently the hydroxyl group at position 3' in one pot is captured by a phosphityl group to prevent position 2' and position 3' transfer of the acyl group.

17 Claims, 2 Drawing Sheets

Specification includes a Sequence Listing.

(56) References Cited

OTHER PUBLICATIONS

Neilands et al., Synthesis of novel tetrathiafulvalene system containing redox-active ribonucleoside and oligoribonucleotide, Org. Lett., 1(13):2065-7 (1999).

Neilands, Dioxo- and aminooxopyrimido-fused tetrathiafulvalenese-base compounds for novel organic semiconductors and for design of sensors for recognition of nucleic acid components, Molecular Crystals and Liquid Crystals Sciene and Technology, Section A: Molecular Crystals and Liquid Crystals, 355:331-49 (2001).

Rozners et al., Oligoribonucleotide analogues containing a mixed backbone of phosphodiester and formacetal internucleoside linkages, together with vicinal 2'-O-methyl groups, ChemBioChem, 8(5):537-45 (2007).

Rozners et al., Solid-phase synthesis of oligoribonucleotides by the H-phosphonate method using 2'-O-benzoyl protective groups, Bioorganicheskaya Khimiya, 14(11):1580-2 (1988).

Rozners et al., Synthesis and properties of oligoribonucleotide analogs having amide (3'-CH2-CO-NH-5') internucleoside linkages, Nucleosides & Nucleotides, 16(7-9):967-70 (1997).

Rozners et al., Synthesis and properties of oligoribonucleotide analogs having formacetal internucleoside linkages, J. Org. Chem., 62(6):1846-50 (1997).

Rozners et al., Synthesis of RNA fragments using the H-phosphonate method and 2'-(2-chlorobenzoyl) protection, Nucleosides & Nucleotides, 14(3-5):855-7 (1995).

STN Search Report, Chemical Abstracts, Database Registry, CAS No. 2073861-46-6 etc. (Feb. 22, 2017).

Chinese Patent Application No. 2017/0051108.5, First Office Action, dated Sep. 3, 2021.

\* cited by examiner

METHOD FOR SYNTHESIZING RIBONUCLEIC ACID H-PHOSPHONATE MONOMER, AND OLIGONUCLEOTIDE SYNTHESIS IN WHICH SAID MONOMER IS USED

INCORPORATION BY REFERENCE OF MATERIAL SUBMITTED ELECTRONICALLY

The Sequence Listing, which is part of the present disclosure, is submitted concurrently with the specification as a text file. The name of the text file containing the Sequence Listing is "53565_Seqlisting.txt", which was created on Dec. 18, 2018 and is 1,800 bytes in size. The subject matter of the Sequence Listing is incorporated herein in its entirety by reference.

TECHNICAL FIELD

The present invention relates to a method of manufacturing, at a low cost, an H-phosphonate nucleoside derivative, which can selectively protect position 2' of a ribonucleoside monomer required for RNA oligonucleotide synthesis.

BACKGROUND ART

Since the discovery of RNAi, RNA oligonucleotides, mainly siRNAs, have had expectation for utilization in pharmaceutical products, and the development thereof is ongoing worldwide.

SUMMARY OF INVENTION

Solution to Problem

As a result of diligent research, the inventors have developed a synthesis method that can readily remove residues of a phosphorous reagent with significantly improved operability by using phosphite as the phosphorous reagent for introducing a phosphorous moiety required for the manufacture of RNA monomers.

The present invention also provides the following items.

(Item 1)

A method of manufacturing a compound represented by the following general formula

[Chemical formula 1]

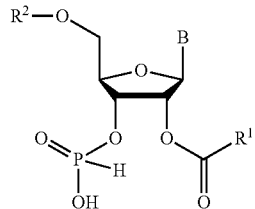

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, or a salt thereof, or solvate thereof, wherein the method comprises:

Step 1 for Reacting

[Chemical formula 2]

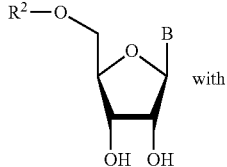

with

[Chemical formula 3]

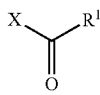

wherein X is a halogen atom, to obtain

[Chemical formula 4]

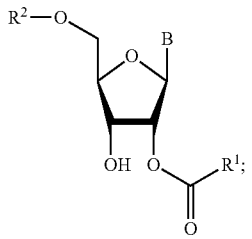

and

Step 2 for Reacting

[Chemical formula 5]

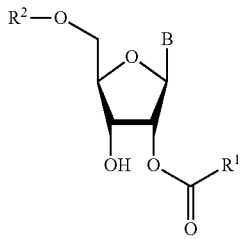

with

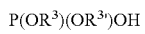

$P(OR^3)(OR^{3'})OH$ wherein $R^3$ and $R^{3'}$ each independently represent a group selected from the group consisting of a substituted or unsubstituted aryl group and a substituted or unsubstituted heteroaryl group, to obtain

[Chemical formula 6]

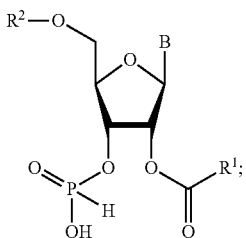

wherein step 1 and step 2 are performed in a single reaction vessel.
(Item 2)
The method of the preceding item, wherein the nucleic acid base that may or may not have a protecting group is selected from the group consisting of

[Chemical formula 7]

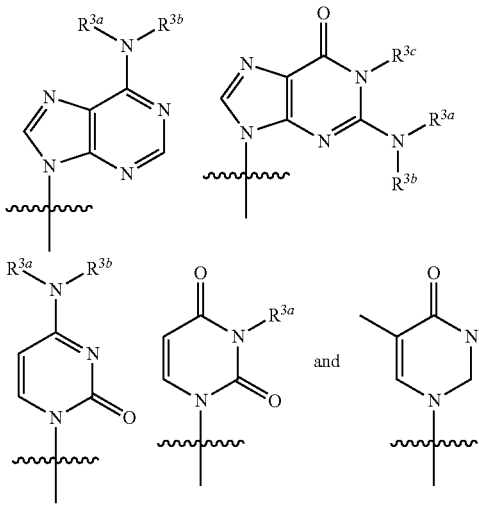

wherein $R^{3a}$, $R^{3b}$, and $R^{3c}$ each independently represent a group selected from the group consisting of a hydrogen atom, a substituted or unsubstituted straight or branched alkylacyl group, a substituted or unsubstituted arylacyl group, a substituted or unsubstituted alkyl group, a substituted or unsubstituted cycloalkyl group, a substituted or unsubstituted aryl group, and a substituted or unsubstituted heteroaryl group, or $R^{3a}$ and $R^{3b}$ are groups together forming an amidine protecting group.
(Item 3)
The method of any one of the preceding items, wherein the amidine protecting group is an N,N-dimethylformamidino group or an N,N-dimethylacetamidino group.
(Item 4)
The method of any one of the preceding items, wherein $R^1$ is a substituted or unsubstituted aryl group.
(Item 5)
The method of any one of the preceding items, wherein the substituted or unsubstituted aryl group is a phenyl group.
(Item 6)
The method of any one of the preceding items, wherein the protecting group of a hydroxy group is a protecting group selected from the group consisting of an ether based protecting group, a silyl ether based protecting group, an acetal based protecting group, and an acyl based protecting group.
(Item 7)
The method of any one of the preceding items, wherein the ether based protecting group is

[Chemical formula 8]

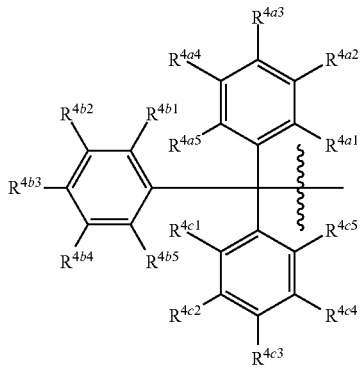

(R2a)

wherein $R^{4a1}$, $R^{4a2}$, $R^{4a3}$, $R^{4a4}$, $R^{4a5}$, $R^{4b1}$, $R^{4b2}$, $R^{4b3}$, $R^{4b4}$, $R^{4b5}$, $R^{4c1}$, $R^{4c2}$, $R^{4c3}$, $R^{4c4}$, and $R^{4c5}$ are each independently a group selected from the group consisting of a hydrogen atom, a substituted or unsubstituted straight or branched alkoxy group, and a substituted or unsubstituted straight or branched alkyl group.
(Item 8)
The method of any one of the preceding items, wherein the substituted or unsubstituted straight or branched alkoxy group is a straight or branched perfluoroalkoxy group.
(Item 9)
The method of any one of the preceding items, wherein the substituted or unsubstituted straight or branched alkyl group is a straight or branched perfluoroalkyl group.
(Item 10)
The method of any one of the preceding items, wherein the silyl ether based protecting group is

[Chemcial formula 9]

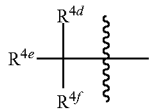

(R2b)

wherein $R^{4d}$, $R^{4e}$, and $R^{4f}$ are each independently a group selected from the group consisting of a substituted or unsubstituted straight or branched alkyl group, a substituted or unsubstituted aryl group, and a substituted or unsubstituted alkenyl group.
(Item 11)
The method of any one of the preceding items, wherein the substituted or unsubstituted alkenyl group is an allyl group.

(Item 12)

The method of any one of the preceding items, wherein the silyl ether based protecting group is

[Chemical formula 10]

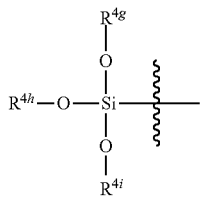

wherein $R^{4g}$, $R^{4h}$, and $R^{4i}$ are each independently a group selected from the group consisting of a substituted or unsubstituted hydrocarbon group, a substituted or unsubstituted silyl group, and a substituted or unsubstituted silyloxyalkyl group.

(Item 13)

The method of any one of the preceding items, wherein the silyl group is substituted with 1 to 3 alkyl groups.

(Item 14)

The method of any one of the preceding items, wherein the substituted or unsubstituted hydrocarbon group is a group selected from the group consisting of a substituted or unsubstituted straight or branched alkyl group, a substituted or unsubstituted straight or branched alkenyl group, a substituted or unsubstituted straight or branched alkynyl group, a substituted or unsubstituted cycloalkyl group, a substituted or unsubstituted cycloalkenyl group, a substituted or unsubstituted aryl group, and a substituted or unsubstituted straight or branched arylalkyl group.

(Item 15)

The method of any one of the preceding items, wherein the substituted or unsubstituted straight or branched alkyl group is a straight or branched haloalkyl group.

(Item 16)

The method of any one of the preceding items, wherein the straight or branched haloalkyl group is a straight or branched perfluoroalkyl group.

(Item 17)

A kit for manufacturing a compound represented by the following general formula

[Chemical formula 13]

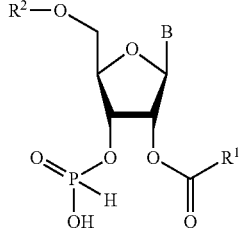

wherein each symbol is synonymous with those recited above, comprising:

[Chemical formula 11]

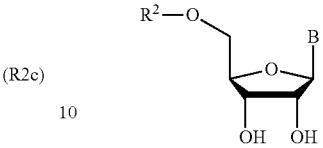

(R2c)

wherein $R^2$ represents a protecting group of a hydroxy group or a hydrogen atom, and B represents a nucleic acid base that may or may not have a protecting group;

[Chemical formula 12]

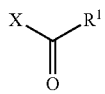

wherein $R^1$ represents a group selected from the group consisting of a substituted or unsubstituted aryl group and a substituted or unsubstituted heteroaryl group, and X is a halogen atom; and

P(OR$^3$) (OR$^{3'}$)OH wherein $R^3$ and $R^{3'}$ each independently represent a group selected from the group consisting of a substituted or unsubstituted aryl group and a substituted or unsubstituted heteroaryl group.

(Item 18)

The kit of the preceding item, wherein the nucleic acid base that may or may not have a protecting group is selected from the group consisting of

[Chemical formula 14]

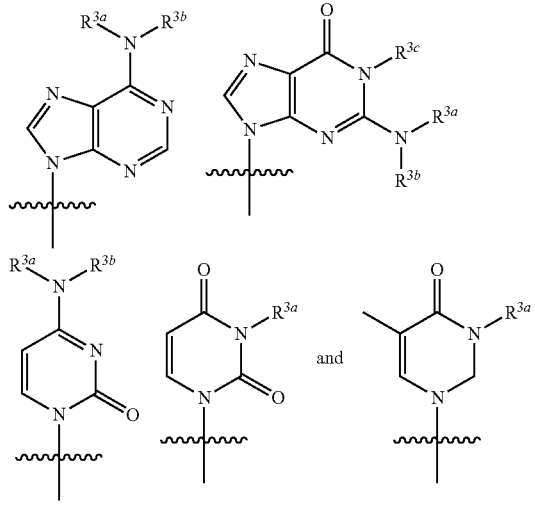

wherein $R^{3a}$, $R^{3b}$, and $R^{3c}$ each independently represent a group selected from the group consisting of a hydrogen atom, a substituted or unsubstituted straight or branched alkylacyl group, a substituted or unsubstituted arylacyl group, a substituted or unsubstituted alkyl group, a substituted or unsubstituted cycloalkyl group, a substituted or unsubstituted aryl group, and a substituted or unsubstituted heteroaryl group, or $R^{3a}$ and $R^{3b}$ are groups together forming an amidine protecting group.

(Item 19)

The kit of any one of the preceding items, wherein the amidine protecting group is an N,N-dimethylformamidino group or an N,N-dimethylacetamidino group.

(Item 20)

The kit of any one of the preceding items, wherein $R^1$ is a substituted or unsubstituted aryl group.

(Item 21)

The kit of any one of the preceding items, wherein the substituted or unsubstituted aryl group is a phenyl group.

(Item 22)

The kit of any one of the preceding items, wherein the protecting group of a hydroxy group is a protecting group selected from the group consisting of an ether based protecting group, a silyl ether based protecting group, an acetal based protecting group, and an acyl based protecting group.

(Item 23)

The kit of any one of the preceding items, wherein the ether based protecting group is

[Chemical formula 15]

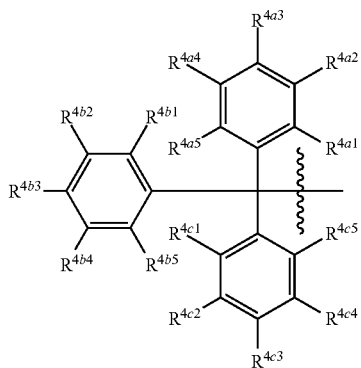

(R2a)

wherein $R^{4a1}$, $R^{4a2}$, $R^{4a3}$, $R^{4a4}$, $R^{4a5}$, $R^{4b1}$, $R^{4b2}$, $R^{4b3}$, $R^{4b4}$, $R^{4b5}$, $R^{4c1}$, $R^{4c2}$, $R^{4c3}$, $R^{4c4}$, and $R^{4c5}$ are each independently a group selected from the group consisting of a hydrogen atom, a substituted or unsubstituted straight or branched alkoxy group, and a substituted or unsubstituted straight or branched alkyl group.

(Item 24)

The kit of any one of the preceding items, wherein the substituted or unsubstituted straight or branched alkoxy group is a straight or branched perfluoroalkoxy group.

(Item 25)

The kit of any one of the preceding items, wherein the substituted or unsubstituted straight or branched alkyl group is a straight or branched perfluoroalkyl group.

(Item 26)

The kit of any one of the preceding items, wherein the silyl ether based protecting group is

[Chemical formula 16]

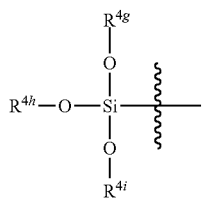

(R2b)

wherein $R^{4d}$, $R^{4e}$, and $R^{4f}$ are each independently a group selected from the group consisting of a substituted or unsubstituted straight or branched alkyl group, a substituted or unsubstituted aryl group, and a substituted or unsubstituted alkenyl group.

(Item 27)

The kit of any one of the preceding items, wherein the substituted or unsubstituted alkenyl group is an allyl group.

(Item 28)

The kit of any one of the preceding items, wherein the silyl ether based protecting group is

[Chemical formula 17]

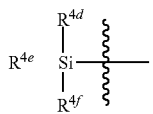

(R2c)

wherein $R^{4g}$, $R^{4h}$, and $R^{4i}$ are each independently a group selected from the group consisting of a substituted or unsubstituted hydrocarbon group, a substituted or unsubstituted silyl group, and a substituted or unsubstituted silyloxyalkyl group.

(Item 29)

The kit of any one of the preceding items, wherein the silyl group is substituted with 1 to 3 alkyl groups.

(Item 30)

The kit of any one of the preceding items, wherein the substituted or unsubstituted hydrocarbon group is a group selected from the group consisting of a substituted or unsubstituted straight or branched alkyl group, a substituted or unsubstituted straight or branched alkenyl group, a substituted or unsubstituted straight or branched alkynyl group, a substituted or unsubstituted cycloalkyl group, a substituted or unsubstituted cycloalkenyl group, a substituted or unsubstituted aryl group, and a substituted or unsubstituted straight or branched arylalkyl group.

(Item 31)

The kit of any one of the preceding items, wherein the substituted or unsubstituted straight or branched alkyl group is a straight or branched haloalkyl group.

(Item 32)

The kit of any one of the preceding items, wherein the straight or branched haloalkyl group is a straight or branched perfluoroalkyl group.

(Item 33)

A phosphorous reagent for selectively manufacturing a compound represented by the following general formula

[Chemical formula 18]

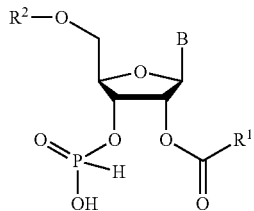

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, comprising:

$P(OR^3)(OR^{3'})OH$ wherein $R^3$ and $R^{3'}$ each independently represent a group selected from the group consisting of a substituted or unsubstituted aryl group and a substituted or unsubstituted heteroaryl group, or a salt thereof, or solvate thereof.

(Item 34)

The phosphorous reagent of the preceding item, wherein the nucleic acid base that may or may not have a protecting group is selected form the group consisting of

[Chemical 19]

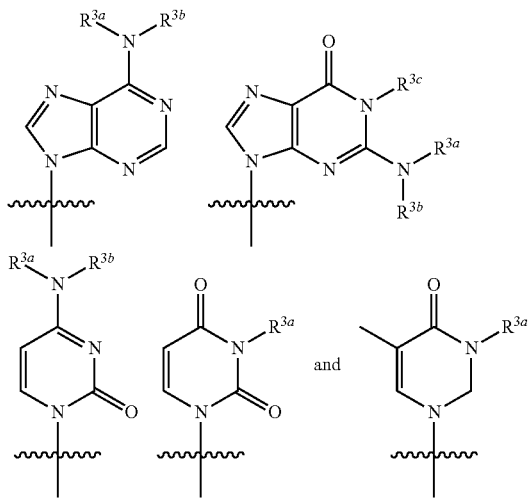

wherein $R^{3a}$, $R^{3b}$, and $R^{3c}$ each independently represent a group selected from the group consisting of a hydrogen atom, a substituted or unsubstituted straight or branched alkylacyl group, a substituted or unsubstituted arylacyl group, a substituted or unsubstituted alkyl group, a substituted or unsubstituted cycloalkyl group, a substituted or unsubstituted aryl group, and a substituted or unsubstituted heteroaryl group, or $R^{3a}$ and $R^{3b}$ are groups together forming an amidine protecting group.

(Item 35)

The phosphorous reagent of any one of the preceding items, wherein the amidine protecting group is an N,N-dimethylformamidino group or an N,N-dimethylacetamidino group.

(Item 36)

The phosphorous reagent of any one of the preceding items, wherein $R^1$ is a substituted or unsubstituted aryl group.

(Item 37)

The phosphorous reagent of any one of the preceding items, wherein the substituted or unsubstituted aryl group is a phenyl group.

(Item 38)

The phosphorous reagent of any one of the preceding items, wherein the protecting group of a hydroxy group is a protecting group selected from the group consisting of an ether based protecting group, a silyl ether based protecting group, an acetal based protecting group, and an acyl based protecting group.

(Item 39)

The phosphorous reagent of any one of the preceding items, wherein the ether based protecting group is

[Chemical formula 20]

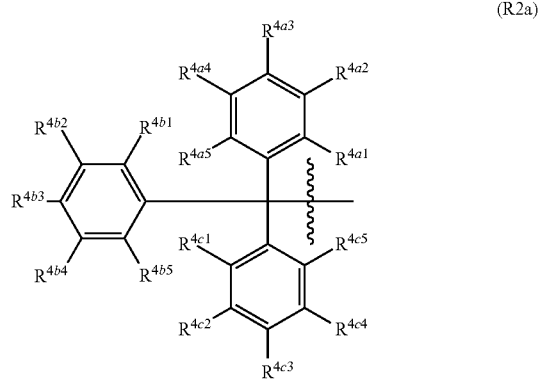

wherein $R^{4a1}$, $R^{4a2}$, $R^{4a3}$, $R^{4a4}$, $R^{4a5}$, $R^{4b1}$, $R^{4b2}$, $R^{4b3}$, $R^{4b4}$, $R^{4b5}$, $R^{4c1}$, $R^{4c2}$, $R^{4c3}$, $R^{4c4}$, and $R^{4c5}$ are each independently a group selected from the group consisting of a hydrogen atom, a substituted or unsubstituted straight or branched alkoxy group, and a substituted or unsubstituted straight or branched alkyl group.

(Item 40)

The phosphorous reagent of any one of the preceding items, wherein the substituted or unsubstituted straight or branched alkoxy group is a straight or branched perfluoroalkoxy group.

(Item 41)

The phosphorous reagent of any one of the preceding items, wherein the substituted or unsubstituted straight or branched alkyl group is a straight or branched perfluoroalkyl group.

(Item 42)

The phosphorous reagent of any one of the preceding items, wherein the silyl ether based protecting group is

[Chemical formula 21]

wherein $R^{4d}$, $R^{4e}$, and $R^{4f}$ are each independently a group selected from the group consisting of a substituted or unsubstituted straight or branched alkyl group, a substituted or unsubstituted aryl group, and a substituted or unsubstituted alkenyl group.

(Item 43)

The phosphorous reagent of any one of the preceding items, wherein the substituted or unsubstituted alkenyl group is an allyl group.

(Item 44)
The phosphorous reagent of any one of the preceding items, wherein the silyl ether based protecting group is

[Chemical formula 22]

(R2c)

wherein $R^{4g}$, $R^{4h}$, and $R^{4i}$ are each independently a group selected from the group consisting of a substituted or unsubstituted hydrocarbon group, a substituted or unsubstituted silyl group, and a substituted or unsubstituted silyloxyalkyl group.

(Item 45)
The phosphorous reagent of any one of the preceding items, wherein the silyl group is substituted with 1 to 3 alkyl groups.

(Item 46)
The phosphorous reagent of any one of the preceding items, wherein the substituted or unsubstituted hydrocarbon group is a group selected from the group consisting of a substituted or unsubstituted straight or branched alkyl group, a substituted or unsubstituted straight or branched alkenyl group, a substituted or unsubstituted straight or branched alkynyl group, a substituted or unsubstituted cycloalkyl group, a substituted or unsubstituted cycloalkenyl group, a substituted or unsubstituted aryl group, and a substituted or unsubstituted straight or branched arylalkyl group.

(Item 47)
The phosphorous reagent of any one of the preceding items, wherein the substituted or unsubstituted straight or branched alkyl group is a straight or branched haloalkyl group.

(Item 48)
The phosphorous reagent of any one of the preceding items, wherein the straight or branched haloalkyl group is a straight or branched perfluoroalkyl group.

(Item 49)
Use of $P(OR^3)(OR^{3'})OH$
wherein $R^3$ and $R^{3'}$ each independently represent a group selected from the group consisting of a substituted or unsubstituted aryl group and a substituted or unsubstituted heteroaryl group,
for selectively manufacturing a compound represented by the following general formula

[Chemical formula 22A]

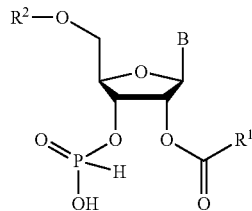

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, or a salt thereof, or solvate thereof.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

The present invention enables the manufacture of a ribonucleic acid H-phosphonate monomer at low cost, resulting in enabling the manufacture of RNA at low cost. The present invention is characterized by reacting hydroxyl groups at positions 2' and 3' having slightly different reactivity with aromatic acyl halide at a low temperature for selective esterification of position 2' and subsequently capturing a hydroxyl group at position 3' with a phosphityl group in one pot to induce transition of positions 2' and 3' of an acyl group.

DESCRIPTION OF EMBODIMENTS

Figure 1:
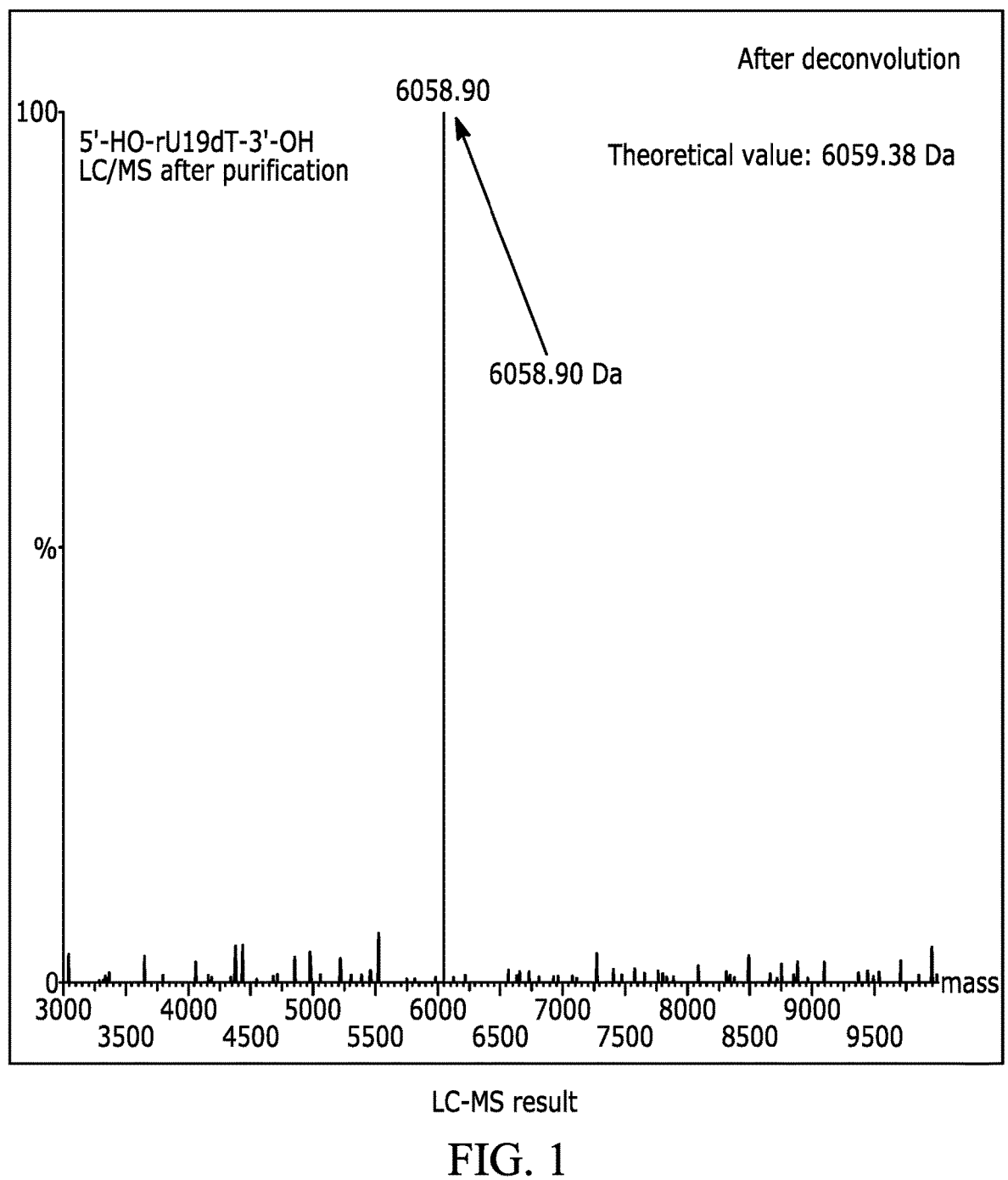
FIG. 1 shows a result of LC-MS analysis on 5'—HO-rU$_{19}$dT-3'—OH.

The present invention is explained hereinafter while presenting the best mode of the invention. Throughout the entire specification, a singular expression should be understood as encompassing the concept thereof in plural form, unless specifically noted otherwise. Thus, singular articles (e.g., "a", "an", "the", and the like in the case of English) should also be understood as encompassing the concept thereof in plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of Terms

The terms used herein are explained below.
As used herein, "substitution" refers to substitution of a specific hydrogen atom of an organic compound with another atom or group of atoms. The atom or group of atoms introduced in place of the hydrogen atom is referred to as a "substituent". All functional groups can be considered a substituent, Examples of substituents include halogen atoms, hydroxy groups, alkyl groups, alkenyl groups, alkynyl groups, cycloalkyl groups, aryl groups, heteroaryl groups, and the like.
"Halogen atom" encompasses fluorine atoms, chlorine atoms, bromine atoms, and iodine atoms.

As used herein, "hydroxy group" refers to a group represented by —OH.

As used herein, a "straight" group refers to a group having a linearly ranging shape, where carbon constituting the group does not branch or form a ring.

As used herein, a "branched" group refers to a group with a structure where two or more carbon atoms are bound to a carbon atom constituting the group.

As used herein, C1, C2 . . . Cn represent the number of carbons, wherein n indicates any positive integer. Thus, C1 is used to represent a substituent with one carbon.

As used herein, "alkyl group" refers to a monovalent group resulting from aliphatic hydrocarbon (alkane) such as methane, ethane, or propane losing one hydrogen atom, and is generally represented by $C_nH_{2n+1}$ wherein n is a positive integer. Examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl, and the like. As used herein, "substituted alkyl group" refers to an alkyl group with H thereof substituted with a substituent defined above.

As used herein, "alkenyl group" refers to a monovalent group resulting from aliphatic hydrocarbon (alkene) having a double bond within the molecule losing a hydrogen atom, and is generally represented by $C_nH_{2n-1}$—, wherein n is a positive integer that is 2 or greater. Examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl, and the like. "Substituted alkenyl group" refers to an alkenyl group with H thereof substituted with a substituent defined above.

As used herein, "allyl group" refers to a group represented by $CH_2=CH-CH_2-$. As used herein, "alkynyl group" refers to a monovalent group resulting from aliphatic hydrocarbon (alkyne) having a triple bond within the molecule losing a hydrogen atom, and is generally represented by $C_nH_{2n-3}$—, wherein n is a positive integer that is 2 or greater. Examples thereof include ethynyl, propynyl, butynyl, pentynyl, hexynyl, heptynyl, octynyl, nonynyl, decynyl, and the like. "Substituted alkynyl group" refers to an alkynyl group with H thereof substituted with a substituent defined above.

As used herein, "cycloalkyl group" refers to alkyl having a cyclic structure. Examples thereof include cyclopropyl, cyclobutyl, cyclopentyl, cyclohexyl, cycloheptyl, cyclooctyl, cyclononyl, cyclodecyl, and the like. "Substituted cycloalkyl group" refers to cycloalkyl with H thereof substituted with a substituent defined above.

As used herein, "cycloalkenyl group" refers to alkenyl having a cyclic structure. Examples thereof include cyclopropenyl, cyclobutenyl, cyclopentenyl, cyclohexenyl, cycloheptenyl, cyclooctenyl, cyclononenyl, cyclodecenyl, and the like. "Substituted cycloalkyl group" refers to cycloalkyl with H thereof substituted with a substituent defined above.

As used herein, "aryl group" refers to a group resulting from a hydrogen atom bound to a ring of an aromatic hydrocarbon leaving. A phenyl group ($C_6H_5$—) is derived from benzene, a tolyl group ($CH_3C_6H_4$—) is derived from toluene, xylyl group (($CH_3)_2C_6H_3$—) is derived from xylene, naphthyl group ($C_{10}H_8$—) is derived from naphthalene, phenanthryl group ($C_{14}H_9$—) is derived from phenanthrene, anthracenyl group ($C_{14}H_9$—) is derived from anthracene, tetracenyl group ($C_{18}H_9$—) is derived from tetracene, chrysenyl group ($C_{18}H_{11}$—) is derived from chrysene, pyrenyl group ($C_{18}H_{11}$—) is derived from pyrene, benzopyrenyl group ($C_{20}H_{11}$—) is derived from benzopyrene, and pentacenyl group ($C_{22}H_{13}$—) is derived from pentacene.

As used herein, "heteroaryl group" refers to a monocyclic aryl group, bicyclic aryl group, or aryl group with more rings having one or more of the same or different heteroatoms selected from any of O, S, and N. Heteroaryl groups with 2 or more rings encompass those in which a ring in the "aryl group" is fused to a monocyclic heteroaryl group, bicyclic heteroaryl group, or heteroaryl group with more rings.

Monocyclic heteroaryl groups are preferably 5- to 8-membered and more preferably 5- to 6-membered. Examples thereof include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl, and the like.

Examples of bicyclic heteroaryl groups include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzoisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl, and the like.

Examples of heteroaryl groups with three or more rings include carbazolyl, acridinyl, xanthenyl, phenothiazinyl, phenoxathiinyl, phenoxazinyl, dibenzofuryl, and the like.

As used herein, "alkoxy group" refers to a group in which the "alkyl group" is bound to an oxygen atom. Examples thereof include methoxy, ethoxy, n-propyloxy, isopropyloxy, n-butyloxy, tert-butyloxy, isobutyloxy, sec-butyloxy, pentyloxy, isopentyloxy, hexyloxy, and the like.

As used herein, "haloalkyl group" refers to a group in which one or more of the "halogen atoms" is bound to the "alkyl group". Examples thereof include monofluoromethyl, monofluoroethyl, monofluoropropyl, 2,2,3,3,3-pentafluoropropyl, monochlormethyl, trifluoromethyl, trichloromethyl, 2,2,2-trifluoroethyl, 2,2,2-trichloroethyl, 1,2-dibromoethyl, 1,1,1-trifluoropropane-2-yl, and the like.

As used herein, "perfluoroalkyl group" refers to an alkyl group in which some or all of the hydrogen bound to carbon of an alkyl group is replaced with fluorine.

As used herein, "perfluoroalkoxy group" refers to an alkoxy group in which some or all of the hydrogen bound to carbon of an alkoxy group is replaced with fluorine.

As used herein, "alkylacyl group" refers to a group in which the "alkyl group" is bound to a carbonyl group. Examples thereof include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl, and the like.

As used herein, "arylacyl group" refers to a group in which the "aryl group" is bound to a carbonyl group. Examples thereof include phenylcarbonyl, naphthylcarbonyl, phenanthrylcarbonyl, anthracenylcarbonyl, and the like.

As used herein, "arylalkyl group" refers to alkyl substituted with one or more of the "aryl groups". Examples thereof include benzyl, phenethyl, phenylpropynyl, benzhydryl, trityl, naphthylmethyl, and the like.

As used herein, "silyl group" refers to a group in which three of the "alkyl group", "alkenyl group", "alkynyl group", or "aryl group" are bound to a silicon atom, where the three groups bound to a silicon atom can be the same or different. Examples thereof include, but are not limited to, trimethylsilyl group (TMS), triethylsilyl group (TES), tert-butyldimethylsilyl group (TBDMS), triisopropylsilyl group (TIPS), tert-butyldiphenylsilyl group (TBDPS), and the like.

As used herein, "silyloxyalkyl group" refers to a group wherein hydrogen on the "alkyl group" is replaced with a "silyloxy group", which is a group where the "silyl group" is bound to an oxygen atom. Examples thereof include, but are not limited to, trimethylsilyloxymethyl group, triethylsilyloxyethyl group, tert-butyldimethylsilyloxymethyl group, triisopropylsilyloxypropyl group, tert-butyldiphenylsilyloxybutyl group, and the like.

As used herein, "cation" refers to an ion having a positive charge. Examples thereof include, but are not limited to, hydrogen ion, quaternary ammonium ion, lithium ion, sodium ion, potassium ion, and the like.

As used herein, "tertiary amine" refers to a compound in which all hydrogens of ammonium are replaced with the "alkyl group" or the "aryl group". Examples thereof include, but are not limited to, trimethylamine, N,N-diisopropylethylamine, tripropylamine, and the like.

As used herein, "nucleic acid base" refers to a base component constituting a nucleic acid. Examples thereof include, but are not limited to, adenine (A), guanine (G), cytosine (C), thymine (T), uracil (U), and the like.

As used herein, "oligomer" refers to a polymer with a low degree of polymerization. The degree of polymerization of an oligomer is, but not limited thereto, 2 to 100.

As used herein, "protecting group" refers to a group used to protect a functional group from a specific chemical reaction.

Examples of protecting groups of a hydroxy group include, but are not limited to, ether based protecting groups (methyl group (Me), benzyl group (Bn), p-methoxybenzyl group (PMB), tert-butyl group (t-Bu), trityl group (Tr), and the like), silyl ether based protecting groups (trimethylsilyl group (TMS), triethylsilyl group (TES), tert-butyldimethylsilyl group (TBDMS), triisopropylsilyl group (TIPS), tert-butyldiphenylsilyl group (TBDPS) and the like), acetal based protecting groups (methoxymethyl group (MOM), 2-tetrahydropyranyl group (THP), ethoxyethyl group (EE) and the like), acyl based protecting groups (acetyl group (Ac), pivaloyl group (Piv), benzoyl group (Bz), and the like), and the like.

Examples of protecting groups of an amino group include, but are not limited to, carbamate based protecting groups (tert-butoxycarbonyl group (Boc), benzyloxycarbonyl group (Cbz), 9-fluorenylmethyloxycarbonyl group (Fmoc), 2,2,2-trichloroethoxycarbonyl group (Troc), allyloxycarbonyl group (Alloc) and the like), amide base protecting groups (trifluoroacetyl group and the like), imide based protecting group (phthaloyl group (Pht) and the like), sulfonamide based protecting groups (p-toluenesulfonyl group (Ts), 2-nitrobenzenesulfonyl group (Ns), and the like), amidine protecting groups (N,N-dimethylformamidino group, N,N-dimethylacetoamidino group, and the like), and the like.

As used herein, "amidine protecting group" is a protecting group represented by the following general formula

[Chemical formula 23]

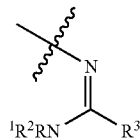

wherein $R^1$, $R^2$, and $R^3$ are each independently a group selected from the group consisting of hydrogen, a substituted or unsubstituted alkyl group, a substituted or unsubstituted cycloalkyl group, a substituted or unsubstituted aryl group, and a substituted or unsubstituted heteroaryl group. Examples thereof include, but are not limited to, N,N-dimethylformamidino group, an N,N-dimethylacetoamidino group, and the like.

As used herein, "solvation" refers to a phenomenon of several solvent molecules surrounding a solute molecule or ion to form a single group.

The compound of the invention can also be provided as a salt. Examples thereof include salts with an organic base (triethylamine or the like), especially trimethylamine. These salts can be formed by a commonly used method. Alternatively, a compound can be produced as a salt (e.g., derived from an additive) depending on the conditions of the manufacturing method of the invention.

The compound of the invention can also be provided as a solvate. Examples thereof include solvates of tertiary amine and water. Such solvates can be formed by a commonly used method. Alternatively, a compound can be produced as a solvate depending on the conditions of the manufacturing method of the invention. A salt of the compound can also be produced and provided as a solvate.

As used herein, "reaction vessel" refers to an apparatus in which a chemical reaction takes place in the manufacturing process of a chemical substance. Examples thereof include, but are not limited to, flasks and beakers.

As used herein, "constituent unit" refers to an atom or a group of atoms constituting a part of the basic structure of an oligomer. This is used synonymously with "monomer".

Explanation of Preferred Embodiments

The preferred embodiments of the present invention are explained hereinafter. It is understood that the embodiments provided hereinafter are provided to facilitate the understanding of the present invention, so that the scope of the present invention should not be limited by the following descriptions. Thus, it is apparent that those skilled in the art can refer to the descriptions herein to make appropriate modifications within the scope of the present invention. It is also understood that the following embodiments of the invention can be used individually or as a combination.

In one aspect, the present invention provides a method of manufacturing a compound represented by the following general formula

[Chemical formula 24]

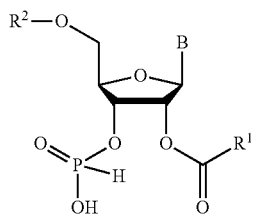

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, or a salt thereof, or solvate thereof, wherein the method comprises:

Step 1 for Reacting

[Chemical formula 25]

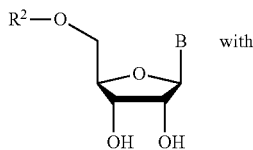

with

[Chemical formula 26]

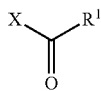

wherein X is a halogen atom, to obtain

[Chemical formula 27]

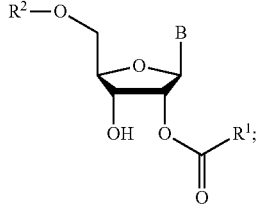

and

Step 2 for Reacting

[Chemical formula 28]

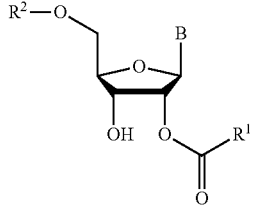

with

P(OR$^3$)(OR$^{3'}$)OH wherein R$^3$ and R$^{3'}$ each independently represent a group selected from the group consisting of a substituted or unsubstituted aryl group and a substituted or unsubstituted heteroaryl group, to obtain

[Chemical formula 29]

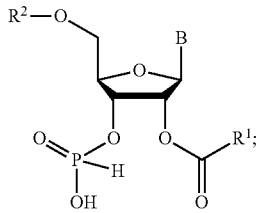

wherein step 1 and step 2 are performed in a single reaction vessel.

For selectively obtaining a position 2' protected ribonucleoside monomer by an organic synthesis reaction, a method of introducing a protecting group to a hydroxy group at position 2' and then introducing a phosphoric acid group to a hydroxy group at position 3' using a phosphorous reagent has been known, as shown in the following formula

[Chemical formula 30]

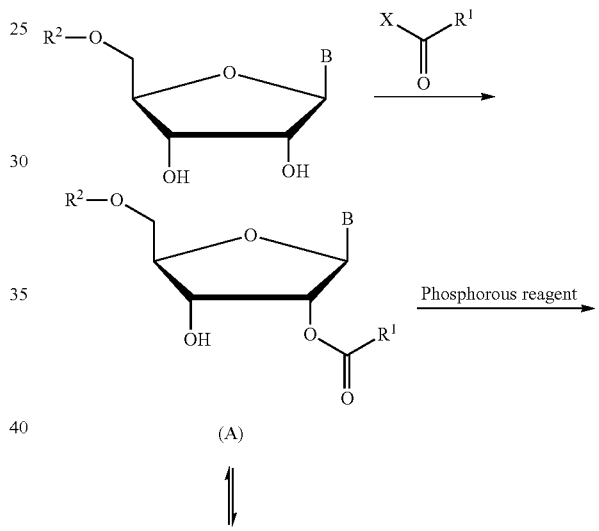

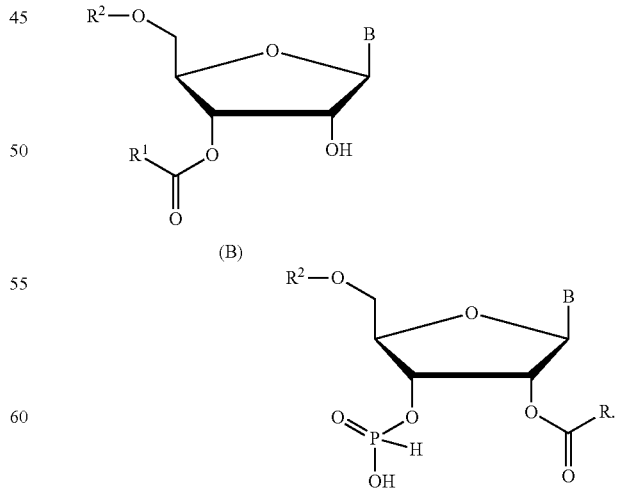

In the above synthesis, intermediate (A) with a protected hydroxy group at position 2' and intermediate (B) with a protected hydroxy group at position 3' are in equilibrium, and the mole ratio of intermediate (A) and intermediate (B) becomes 50/50 over time. Thus, a reaction for introducing a phosphoric acid group needs to be performed quickly. For this reason, it was necessary to use a phosphorous reagent with a very high reactivity.

However, phosphorous reagents with a very high reactivity are generally difficult to handle, with strong toxicity, instability at room temperature, etc. Some phosphorous reagents have problems of being labor-intensive with respect to purification, e.g., the need to increase the number of column chromatography runs due to the difficulty in removing residuals of the reagent (e.g., phosphoric acid) or the like.

The present invention used phosphonate, which has relatively low reactivity, as a phosphorous reagent to unexpectedly find that a protecting group can be selectively introduced to a hydroxy group at position 2' and a phosphonate residue can be readily removed from a reaction product. Since this enables phosphonate residue to be readily removed, the purity of position 2' protected ribonucleotide monomer has improved compared to conventional methods.

A greater variety of position 2' protected ribonucleotide monomers can also be synthesized due to the expanded substrate specificity in comparison to conventional methods using enzymes.

In a preferred embodiment, step 1 is performed at a low temperature below room temperature. The reaction temperature at this time is, but not limited to, −40 to 20° C., −40 to 15° C., −40 to 10° C., −40 to 5° C., −40 to 0° C., −40 to −10° C., −40 to −20° C., −40 to −30° C., −30 to 20° C., −20 to 20° C., −10 to 20° C., 0 to 20° C., or 5 to 20° C., and preferably −40 to 20° C. Although not wishing to be bound by any theory, this is because progression of an isomerization reaction of intermediate (A) and intermediate (B) results in the mole ratio of intermediate (A) and intermediate (B) to be 50/50 depending on the base or solvent. It has been revealed that even if a reaction is performed at room temperature or a temperature thereabove, very little isomerization occurs in a short period of time (several hours), but the isomerization reaction progresses at room temperature or a temperature thereabove under a specific condition (e.g., when concentrated). Even if an isomerization reaction progressed, this is acceptable up to about 10% because this can be removed by purification after phosphonation.

In a preferred embodiment, step 2 is performed within 1 minutes, 2 minutes, 3 minutes, 4 minutes, 5 minutes, 10 minutes, 20 minutes, 30 minutes, 40 minutes, 50 minutes, 1 hour, 2 hours, 3 hours, or 4 hours after the completion of step 1, and preferably within 1 hour after the completion.

It is possible to confirm whether step 1 has been completed by thin-layer chromatography (TLC) or liquid chromatography, but confirmation means is not limited thereto. If a preliminary experiment is conducted in advance so that the time at which step 1 is completed can be estimated, step 2 can be performed without confirming whether step 1 has been completed.

In a preferred embodiment, the temperature in a reaction system upon performing step 2 is, but not limited to, −40 to 25° C., −40 to 20° C., −40 to 10° C., −40 to 5° C., −40 to 0° C., −40 to −10° C., −40 to −20° C., −40 to −30° C., −30 to 25° C., −20 to 25° C., −10 to 25° C., 0 to 25° C., 5 to 25° C., 10 to 25° C., 20 to 25° C., −30 to 20° C., −20 to 20° C., −10 to 20° C., 0 to 20° C., 5 to 20° C., or 10 to 20° C., and preferably −20 to 20° C.

In a preferred embodiment, it is preferable to add a base before adding phosphite in step 2. Although not wishing to be bound by any theory, this is for quenching an excessive amount of acyl halide added in step 1. The base added at this time is not limited, but dimethylamine hydrochloride is preferred. The time until adding phosphite after adding a base is, but is not limited to, 30 minutes, 1 hour, 2 hours, 3 hours, or 4 hours. The temperature at which a base is added is, but not limited to, −40° C. to room temperature, −40 to 30° C., −40 to 20° C., −40 to 10° C., −40 to 5° C., −40 to 0° C., −40 to −10° C., −40 to −20° C., −40 to −30° C., −30 to 30° C., −20 to 30° C., −10 to 30° C., 0 to 30° C., 5 to 30° C., 10 to 30° C., or 20 to 30° C., and preferably −40° C. to room temperature or −40 to 0° C.

Since a product obtained from the reaction of the invention has higher pre-purification purity than those obtained by a conventional reaction, subsequent purification can be more readily performed than those obtained by a conventional reaction.

In a preferred embodiment, the nucleic acid base that may or may not have a protecting group is selected from the group consisting of

[Chemical 31]

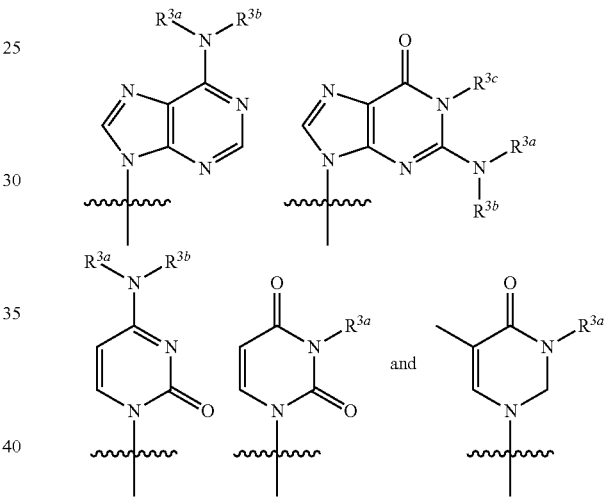

wherein $R^{3a}$, $R^{3b}$, and $R^{3c}$ each independently represent a group selected from the group consisting of a hydrogen atom, a substituted or unsubstituted straight or branched alkylacyl group, a substituted or unsubstituted arylacyl group, a substituted or unsubstituted alkyl group, a substituted or unsubstituted cycloalkyl group, a substituted or unsubstituted aryl group, and a substituted or unsubstituted heteroaryl group, or $R^{3a}$ and $R^{3b}$ are groups together forming an amidine protecting group. In a more preferred embodiment, the amidine protecting group is an N,N-dimethylformamidino group or an N,N-dimethylacetamidino group. The reaction of the invention progresses position 2' selectively not only when the nucleic acid base is a purine base, but also when it is a pyrimidine base.

In a preferred embodiment, $R^1$ is a substituted or unsubstituted aryl group. In a more preferred embodiment, the substituted or unsubstituted aryl group is a phenyl group. Although not wishing to be bound by any theory, this is because the reaction would progress position 2' selectively in a reaction of step 1.

In a preferred embodiment, the protecting group of a hydroxy group is a protecting group selected from the group consisting of an ether based protecting group, a silyl ether based protecting group, an acetal based protecting group, and an acyl based protecting group. Position 2' selective reaction progresses by using any of the protecting groups.

In a more preferred embodiment, the ether based protecting group is

[Chemical formula 32]

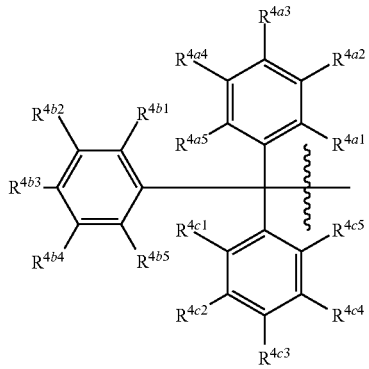

(R2a)

wherein $R^{4a1}$, $R^{4a2}$, $R^{4a3}$, $R^{4a4}$, $R^{4a5}$, $R^{4b1}$, $R^{4b2}$, $R^{4b3}$, $R^{4b4}$, $R^{4b5}$, $R^{4c1}$, $R^{4c2}$, $R^{4c3}$, $R^{4c4}$, and $R^{4c5}$, are each independently a group selected from the group consisting of a hydrogen atom, a substituted or unsubstituted straight or branched alkoxy group, and a substituted or unsubstituted straight or branched alkyl group. Although not wishing to be bound by any theory, the leaving capability can be adjusted by changing a substituent on a phenyl group.

In a more preferred embodiment, the substituted or unsubstituted straight or branched alkoxy group is a straight or branched perfluoroalkoxy group, and the substituted or unsubstituted straight or branched alkyl group is a straight or branched perfluoroalkyl group. Although not wishing to be bound by any theory, this is because a product of interest and a protecting group after deprotection can be readily separated/purified by using a fluorine containing solvent.

In a more preferred embodiment, the silyl ether based protecting group is

[Chemical formula 33]

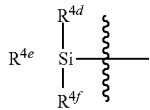

(R2b)

wherein $R^{4d}$, $R^{4e}$, and $R^{4f}$ are each independently a group selected from the group consisting of a substituted or unsubstituted straight or branched alkyl group, a substituted or unsubstituted aryl group, and a substituted or unsubstituted alkenyl group. In a more preferred embodiment, the substituted or unsubstituted alkenyl group is an allyl group. Although not wishing to be bound by any theory, leaving capability can be adjusted by changing a substituted on a silicon atom.

In a more preferred embodiment, the silyl ether based protecting group is

[Chemical formula 34]

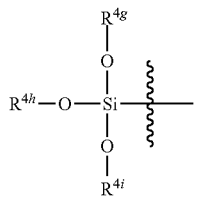

(R2c)

wherein $R^{4g}$, $R^{4h}$, and $R^{4i}$ are each independently a group selected from the group consisting of a substituted or unsubstituted hydrocarbon group, a substituted or unsubstituted silyl group, and a substituted or unsubstituted silyloxyalkyl group. In a more preferred embodiment, the silyl group is substituted with 1 to 3 alkyl groups. Although not wishing to be bound by any theory, leaving capability can be adjusted by changing a substituent.

In a more preferred embodiment, the substituted or unsubstituted hydrocarbon group is a group selected from the group consisting of a substituted or unsubstituted straight or branched alkyl group, a substituted or unsubstituted straight or branched alkenyl group, a substituted or unsubstituted straight or branched alkynyl group, a substituted or unsubstituted cycloalkyl group, a substituted or unsubstituted cycloalkenyl group, a substituted or unsubstituted aryl group, and a substituted or unsubstituted straight or branched arylalkyl group.

In a more preferred embodiment, the substituted or unsubstituted straight or branched alkyl group is a straight or branched haloalkyl group. In a more preferred embodiment, the straight or branched haloalkyl group is a straight or branched perfluoroalkyl group. Although not wishing to be bound by any theory, this is because a product of interest and a protecting group after deprotection can be readily separated/purified by using a fluorine containing solvent.

In one aspect, the present invention provides a kit for manufacturing a compound represented by the following general formula

[Chemical formula 37]

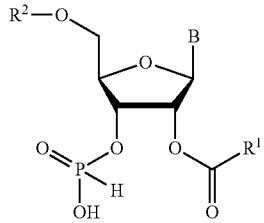

wherein each symbol is synonymous with those recited above, comprising:

[Chemical formula 35]

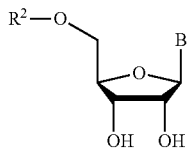

wherein $R^2$ represents a protecting group of a hydroxy group or a hydrogen atom, and B represents a nucleic acid base that may or may not have a protecting group;

[Chemical formula 36]

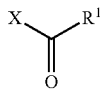

wherein $R^1$ represents a group selected from the group consisting of a substituted or unsubstituted aryl group and a substituted or unsubstituted heteroaryl group, and X is a halogen atom; and

P(OR$^3$)(OR$^{3'}$)OH wherein $R^3$ and $R^{3'}$ each independently represent a group selected from the group consisting of a substituted or unsubstituted aryl group and a substituted or unsubstituted heteroaryl group. Although not wishing to be bound by any theory, this is because phosphorous reagent residue can be readily removed upon purification when synthesizing a position 2' protected ribonucleoside monomer using the kit, so that a position 2' protected ribonucleoside monomer with high purity can be more readily obtained.

In one aspect, the present invention provides a phosphorous reagent for selectively manufacturing a compound represented by the following general formula

[Chemical formula 38]

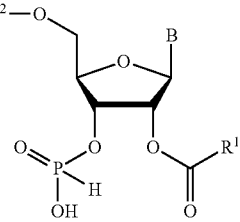

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, comprising:

P(OR$^3$)(OR$^{3'}$)OH wherein $R^3$ and $R^{3'}$ each independently represent a group selected from the group consisting of a substituted or unsubstituted aryl group and a substituted or unsubstituted heteroaryl group, or a salt thereof, or solvate thereof. Although not wishing to be bound by any theory, the "selectively manufacturing" refers to the proportion of product of interest in the entire reaction product being 1/X or greater than 1/X when X products are expected to be producable. For example, when 2 products are expected to be producable, the proportion of the product of interest in the entire reaction product is 50% (=½) or greater than 50%, preferably 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or greater.

General Synthesis Method of Ribonucleic Acid H-phosphonate Monomer

[Chemical formula 39]

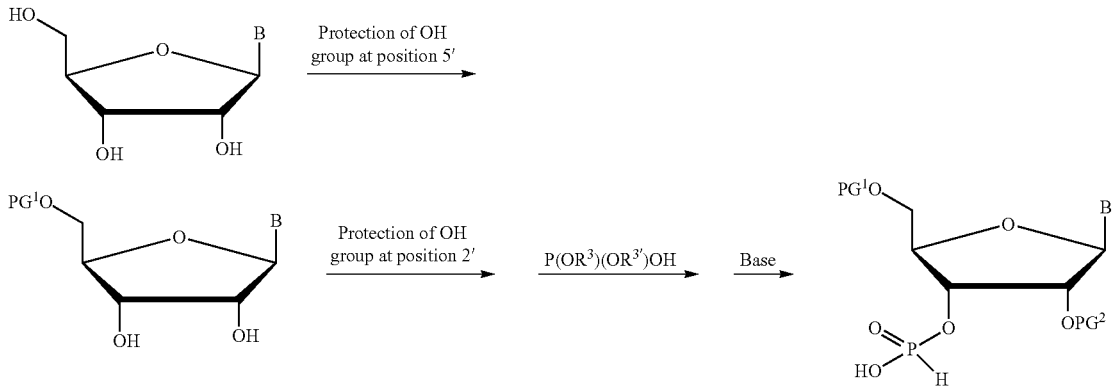

In the scheme, PG$^1$ and PG$^2$ represent a protecting group of any hydroxyl group, R$^3$ and R$^{3'}$ represent a group selected from the group consisting of a substituted or unsubstituted aryl group and a substituted or unsubstituted heteroaryl group, and B represents a nucleic acid base that may or may not have a protecting group.

(1) Synthesis of Position 5' Protected Nucleoside

Under an inert gas (e.g., nitrogen) atmosphere, a nucleoside (e.g., 5.34 g (20 mmol) of adenosine) and a suitable reaction solvent (e.g., 400 mL of pyridine) are placed in a suitable reaction vessel (e.g., three neck flask (500 mL)) and stirred at a suitable reaction temperature (e.g., 0° C.). A suitable protection reagent (e.g., 40 mL of dichloromethane solution of 3.07 g (20.4 mmol) of t-butylchlorodimethylsilane) is added (e.g., by slowly dripping), and the mixture is stirred for a suitable time at a suitable temperature (e.g., 12 hours at room temperature) under an inert gas (e.g., nitrogen) atmosphere. The reaction solvent is evaporated, and water (e.g., 100 mL) and organic solvent (e.g., 100 mL of chloroform/40 mL of methanol) are added to the resulting residue for extraction. The organic layer is evaporated under reduced pressure (e.g., after one more extraction of the aqueous layer with 100 mL of chloroform). The resulting mixture is purified (e.g., in a silica gel column) and the fraction of interest is concentrated under reduced pressure to obtain a product of interest (e.g., white solid).

(2) Synthesis of Ribonucleic Acid H-phosphonate Monomer

Under an inert gas (e.g., nitrogen) atmosphere, a position 5' protected nucleoside (e.g., 3.82 g (10 mmol) of t-butyldimethylsilyl protected adenosine) and a suitable solvent (e.g., 100 mL of pyridine) are placed in a suitable reaction vessel (e.g., three neck flask (300 mL)) and stirred at a suitable reaction temperature (e.g., -40° C.). A suitable protection reagent (e.g., 10 mL of dichloromethane solution of 2.11 g (15 mmol) of benzoyl chloride) is added (e.g., by slowly dripping over 30 minutes), and the mixture is stirred for a suitable time at a suitable temperature (e.g., 3 hours at -40° C.). A suitable reagent (e.g., 489 mg (6 mmol) of dimethylamine hydrochloride) is added, the temperature is raised (e.g., from -40° C. to room temperature by detaching a cooling trough), and the resulting mixture is stirred for a suitable time (e.g., 2 hours) after adding the reagent. A suitable phosphorous reagent (e.g., 20 mL of pyridine solution of 7.03 g (30 mmol) of diphenyl phosphite) is added (e.g., by slowing dripping) at a suitable temperature (e.g., room temperature) and stirred for a suitable time at a suitable temperature (e.g., 3 hours at room temperature). After adding a suitable base (e.g., 10 mL of triethylamine and 10 mL of water), the mixture is further stirred for a suitable time at a suitable temperature (e.g., 1 hour at room temperature). The reaction solvent (e.g., pyridine, dichloromethane) is evaporated under reduced pressure, and water (e.g., 100 mL) is added to the resulting residue for extraction (e.g., twice) with an organic solvent (e.g., 100 mL of chloroform). After washing the resulting organic layer (e.g., by adding 4 mL of triethylamine and 100 mL of water), the organic solvent (e.g., chloroform) is evaporated under reduced pressure. The resultant is purified (e.g., in a silica gel column by adding 0.5 mL of triethylamine to the crude product) and the fraction of interest is concentrated under reduced pressure to obtain a product of interest (e.g., white solid).

(3) Synthesis of Oligonucleotide

An oligonucleotide is synthesized by performing an elongation reaction (e.g., with liquid phase synthesis) using a starting base (5'—OH-dT-3'—O-suc-O-PEG), monomer (e.g., TBDMS-rU-H-phosphonate (1.3 equivalent)), condensing agent (e.g., pivaloyl chloride (6.5 equivalent)), oxidizing agent (e.g., 0.1M I$_2$ (1.5 equivalent)), and desilylation agent (tetra-n-butylammonium fluoride (TBAF) (15 equivalent)) at a suitable reaction temperature (e.g., 25° C.) in a suitable reaction solvent (e.g., pyridine: MeCN=1:1 (0.05 M)), and purifying (e.g., by ether precipitation) upon each elongation. After elongation to a desired degree of polymerization (e.g., degree of polymerization of 20), and then deprotection of a polymer of a position 3' hydroxy group and a protecting group of a position 2' hydroxy group with a suitable reagent (e.g., ethylenediamine), a desired oligonucleotide is obtained (e.g., by additional HPLC purification). Furthermore, after deprotection of a protecting group of a position 5' hydroxy group (e.g., TBDMS group) with a suitable reagent (e.g., TBAF), a desired oligonucleotide is obtained (e.g., by additional HPLC purification).

Reference literatures such as scientific literatures, patents, and patent applications cited herein are incorporated herein by reference to the same extent that the entirety of each document is specifically described.

The present invention has been explained while showing preferred embodiments to facilitate understanding. The present invention is explained hereinafter based on Examples. The aforementioned explanation and the following Examples are not provided to limit the present invention, but for the sole purpose of exemplification. Thus, the scope of the present invention is not limited to the embodiments and Examples that are specifically described herein and is limited only by the scope of claims.

EXAMPLES

The present invention is more specifically explained according to the following Examples/Comparative Examples, but the present invention should not to be interpreted to be limited thereto. Examples obtained by appropriate combination of technical means disclosed in each Example are also encompassed within the scope of the present invention. The compound names indicated in the following Examples and Comparative Examples are not necessarily in accordance with the IUPAC nomenclature of organic chemistry.

The abbreviations used herein have the following meaning.

Bu: Butyl
Et: Ethyl
d: Deoxy (DNA)
HPLC: High performance liquid chromatography
Me: Methyl
NMR: Nuclear magnetic resonance
PEG: Polyethylene glycol
Ph: Phenyl
r: Ribose (RNA)
suc: Succinic acid
TBAF: Tetra-n-butylammonium fluoride
TBDMS: tert-butyldimethylsilyl
t-Bu: Tertiary butyl
THF: Tetrahydrofuran
X: Halogen group NMR spectra were measured with Bruker's AVANCE III 400.

(Reference Example 1) Examination of Conditions for Position 2' Selective Esterification Reaction Using Adenosine

[Chemical formula 40]

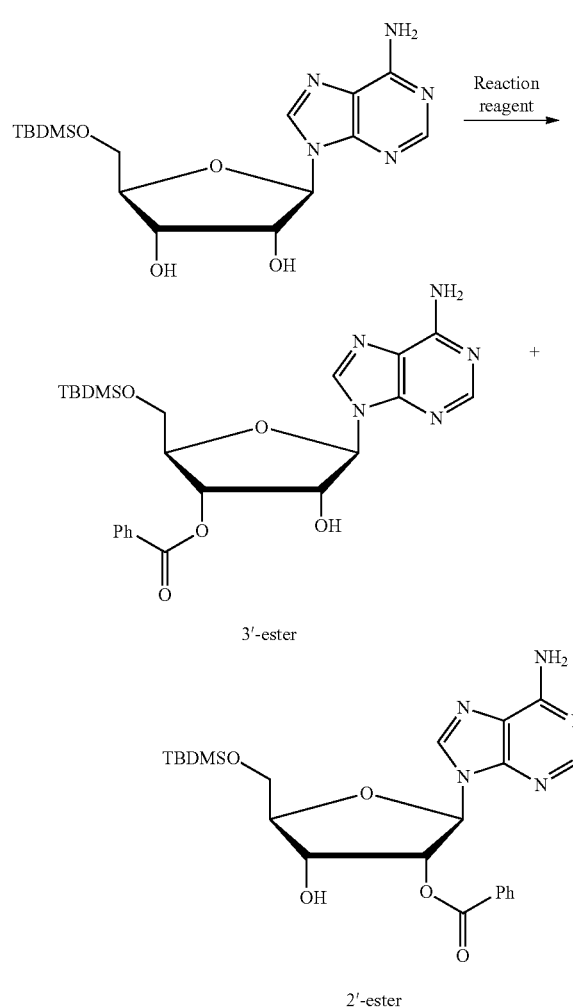

The conditions for benzoylation of t-butyldimethylsilyl group protected adenosine tin acetal were examined. Since 2'-ester and 3'-ester can be separated in a silica gel column, purification was performed, and isolation yield was found from the production ratio.

TABLE 1

| Reaction reagent | Equivalent | 3'-PhCO (%) | 2'-PhCO (%) |
|---|---|---|---|
| (PhCO)$_2$O | 1.5 eq. | 52% | 29% |
| PhCO—Cl | 1.5 eq. | 28% | 70% |
| Bu$_2$SnO<br>PhCO—Cl | 1.0 eq.<br>1.5 eq. | 36% | 39% |
| Ph$_2$B—OCH$_2$CH$_2$NH$_2$<br>PhCO—Cl | 0.1 eq.<br>1.5 .eq | 30% | 38% |

When benzoic anhydride was used as a reagent, position 3' protected esters were prioritized. When benzoyl chloride was used, position 2' protected esters of interest were prioritized. For a reaction using tin acetal or borinic acid ester as a promoter to attempt a more selective reaction, a decrease in selectivity was observed.

It was found that concentration of a reaction solution under reduced pressure at room temperature or above resulted in isomerization to 50/50 in mole ratio.

In view of the above result, synthesis of phosphonates by a one-pot method was able to solve the problem of isomerization, and enabled the compound of interest, adenosine monomer, to be obtained at an excellent yield.

(Example 1) Synthesis of Ribonucleic Acid H-phosphonate Monomer (1) Synthesis Method of Adenosine Monomer

[Chemical formula 42]

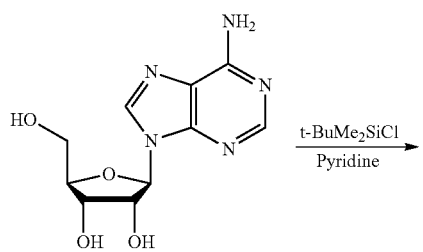

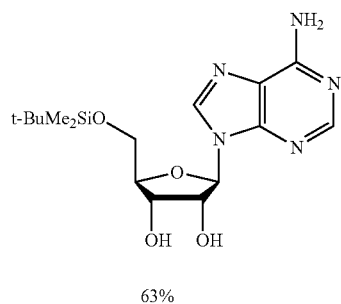

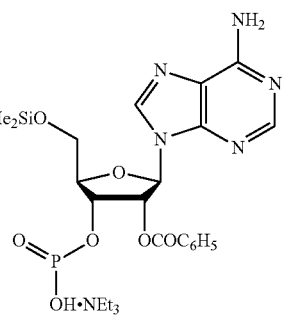

(1-1) Synthesis of 5'-t-butyldimethylsiyl Adenosine

Under a nitrogen atmosphere, 5.34 g (20 mmol) of adenosine and 400 mL of pyridine were placed in a three neck flask (500 mL) and stirred at 0° C. 40 mL of dichloromethane solution of 3.07 g (20.4 mmol) of t-butylchlorodimethylsilane was slowly dripped in, and the mixture was stirred for 12 hours at room temperature under a nitrogen atmosphere. The pyridine and dichloromethane were evaporated, and 100 mL of water and 100 mL of chloroform/40 mL of methanol were added to the resulting residue for extraction. The organic layer was evaporated under reduced pressure after one more extraction of the aqueous layer with 100 mL of chloroform. The resulting mixture was purified in a silica gel column and the fraction of interest was concentrated under reduced pressure to obtain a white solid at 4.80 g (yield of 63%).

(1-2) Synthesis of 5'-t-butyldimethylsilyl-2'-benzoyladenosine-3'-H-phosphonate Under a nitrogen atmosphere, 3.82 g (10 mmol) of t-butyldimethylsilyl protected adenosine and 100 mL of pyridine were placed in a three neck flask (300 mL) and stirred at −40° C. 10 mL of dichloromethane solution of 2.11 g (15 mmol) of benzoyl chloride was slowly dripped in over 30 minutes, and the mixture was stirred for 3 hours at −40° C. under a nitrogen atmosphere. 489 mg (6 mmol) of dimethylamine hydrochloride was added to the reaction solution, the temperature was raised from −40° C. to room temperature by detaching a cooling trough, and the resulting mixture was stirred for 2 hours after adding dimethylamine hydrochloride. 20 mL of pyridine solution of 7.03 g (30 mmol) of diphenyl phosphite was slowly dripped in at 20° C., and the mixture was stirred for 3 hours at room temperature under a nitrogen atmosphere. After adding 10 mL of triethylamine and 10 mL of water, the mixture was further stirred for 1 hour at room temperature. The pyridine and dichloromethane were evaporated under reduced pressure, and 100 mL of water was added to the resulting residue for extraction, twice with 100 mL of chloroform. After adding 4 mL of triethylamine and 100 mL of water, and washing, the resulting organic layer, the chloroform was evaporated under reduced pressure. The product of interest was purified in a silica gel column by adding 0.5 mL of triethylamine to the crude product and the fraction of interest was concentrated under reduced pressure to obtain a white solid at 4.23 g (yield of 65%).

$^1$H NMR (400 MHz, CDCl$_3$), σ0.098 (6H, d), σ0.907 (9H, s), σ1.363 (9H, t, J=7.6 Hz), σ2.628-2.754 (2H, m), σ3.095 (6H, q, J=7.6 Hz), σ3.915 (2H, ddd), σ4.341 (1H, q), σ4.964-5.007 (1H, m), σ5.798 (2H, br), σ6.546 (1H, dd), σ6.975 (1H, d, $J_{pH}$=617 Hz), σ8.224 (1H, s), σ8.324 (1H, s).

$^{31}$P NMR (162 MHz, CDCl$_3$), σ3.57

(2) Synthesis Method of Uridine Monomer

[Chemical formula 43]

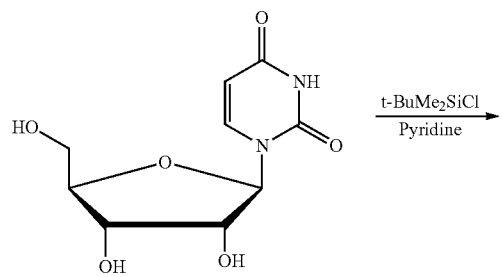

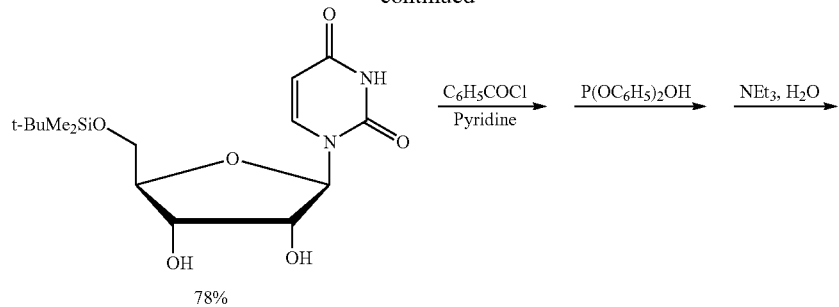

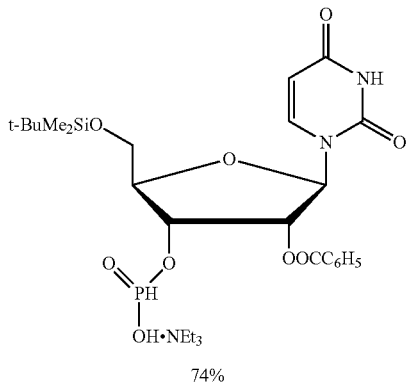

(2-1) Synthesis of 5'-t-butyldimethylsilyl Uridine

Under a nitrogen atmosphere, 4.88 g (20 mmol) of uridine and 40 mL of pyridine were placed in a three neck flask (100 mL) and stirred at 0° C. 40 mL of dichloromethane solution of 3.07 g (20.4 mmol) of t-butylchlorodimethylsilane was slowly dripped in, and the mixture was stirred for 12 hours at room temperature under a nitrogen atmosphere. The pyridine and dichloromethane were evaporated under reduced pressure, and 100 mL of water was added to the resulting residue for extraction, twice with 100 mL of chloroform. The chloroform was evaporated under reduced pressure. The resulting mixture was purified in a silica gel column and the fraction of interest was concentrated under reduced pressure to obtain a white solid at 5.59 g (yield of 78%).

(2-2) Synthesis of 5'-t-butyldimethylsilyl-2'-benzoyluridine-3'—H-phosphonate

Under a nitrogen atmosphere, 3.58 g (10 mmol) of t-butyldimethylsilyl protected uridine and 100 mL of pyridine were placed in a three neck flask (300 mL) and stirred at −40° C. 10 mL of dichloromethane solution of 2.11 g (15 mmol) of benzoyl chloride was slowly dripped in over 30 minutes, and the mixture was stirred for 3 hours at −40° C. under a nitrogen atmosphere. 489 mg (6 mmol) of dimethylamine hydrochloride was added to the reaction solution, the temperature was raised from −40° C. to room temperature by detaching a cooling trough, and the resulting mixture was stirred for 2 hours after adding dimethylamine hydrochloride. 20 mL of pyridine solution of 7.03 g (30 mmol) of diphenyl phosphite was slowly dripped in at 20° C., and the mixture was stirred for 3 hours at room temperature under a nitrogen atmosphere. After adding 10 mL of triethylamine and 10 mL of water, the mixture was stirred for 1 hour at room temperature. The pyridine and dichloromethane were evaporated under reduced pressure, and 100 mL of water was added to the resulting residue for extraction, twice with 100 mL of chloroform. After adding 4 mL of triethylamine and 100 mL of water, and washing, the chloroform layer, the chloroform was evaporated under reduced pressure. The resultant was purified in a silica gel column by adding 0.5 mL of triethylamine to the crude product to obtain a white solid at 6.27 g (yield of 74%). $^1$H NMR (400 MHz, CDCl$_3$), σ0.101 (6H, d, J=3.2 Hz), σ0.902 (9H, s), σ1.368 (9H, t, J=7.6 Hz), σ2.055 (1H, q), σ2.52-2.58 (1H, dd), σ3.092 (6H, q, J=7.2 Hz), σ3.874 (2H, t, J=12.8 Hz), σ4.265 (1H, s), σ4.864 (1H, t, J=6.8 Hz), σ6.324 (1H, t, J=6.4 Hz), σ7.018 (1H, d, J$_{pH}$=627 Hz), σ7.424 (1H, br), σ7.158 (1H, s), σ8.377 (1H, br).
$^{31}$P NMR (162 MHz, CDCl$_3$), σ2.99

(3) Synthesis Method of Cytidine Monomer

[Chemical formula 44]

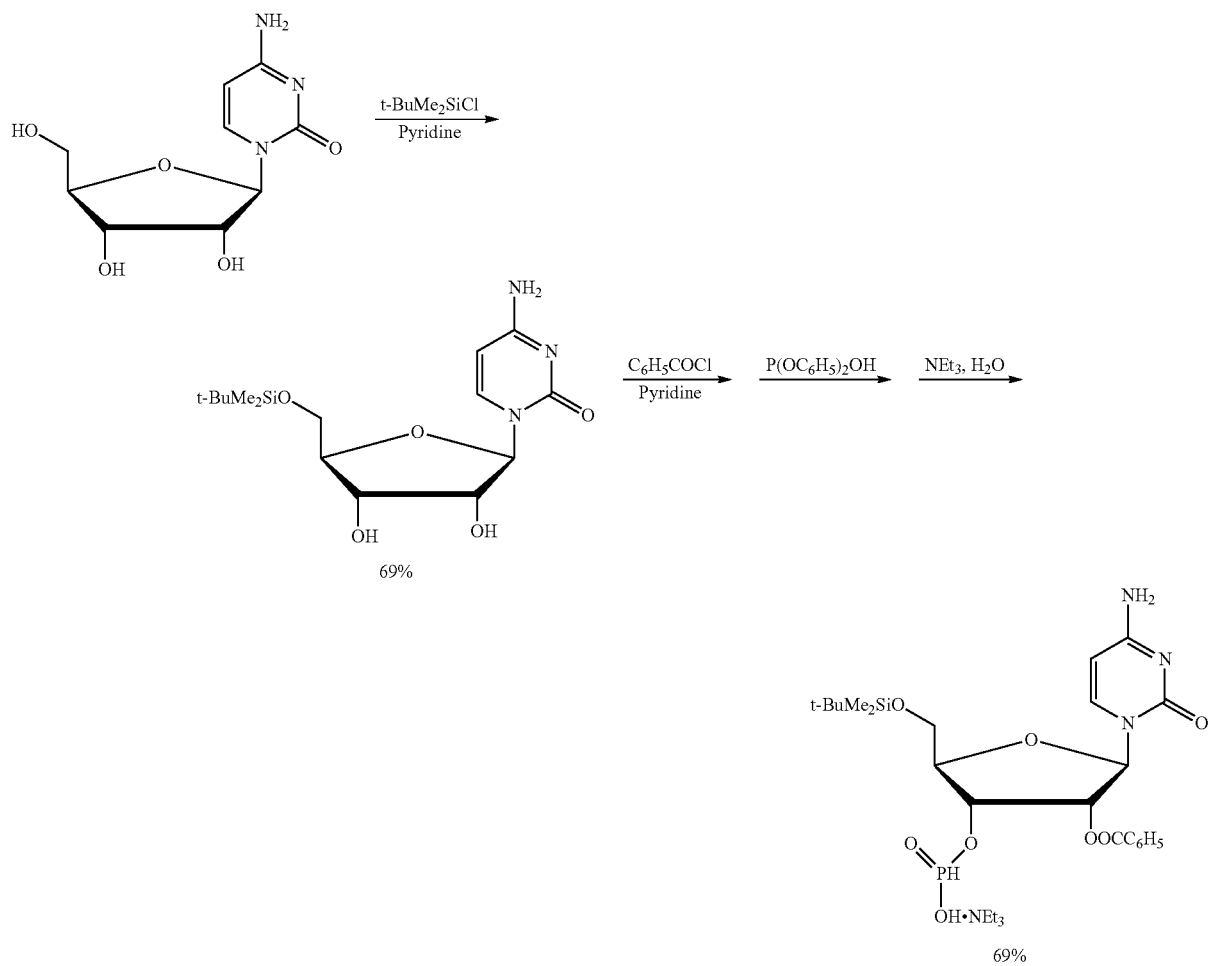

(3-1) Synthesis of 5'-t-butyldimethylsilyl Cytidine

Under a nitrogen atmosphere, 4.86 g (20 mmol) of cytidine and 400 mL of pyridine were placed in a three neck flask (500 mL) and stirred at 0° C. 40 mL of dichloromethane solution of 3.07 g (20.4 mmol) of t-butylchlorodimethylsilane was slowly dripped in, and the mixture was stirred for 12 hours at room temperature under a nitrogen atmosphere. The pyridine and dichloromethane were evaporated under reduced pressure, and 100 mL of water was added to the resulting residue for extraction, twice with 100 mL of chloroform. The organic layer was evaporated under reduced pressure. The resulting mixture was purified in a silica gel column to obtain a white solid at 4.93 g (yield of 69%).

(3-2) Synthesis of 5'-t-butyldimethylsilyl-2'-benzoylcytidine-3'—H-phosphonate

Under a nitrogen atmosphere, 3.57 g (10 mmol) of t-butyldimethylsilyl protected cytidine and 100 mL of pyridine were placed in a three neck flask (300 mL) and stirred at −40° C. 10 mL of dichloromethane solution of 2.11 g (15 mmol) of benzoyl chloride was slowly dripped in over 30 minutes, and the mixture was stirred for 3 hours at −40° C. under a nitrogen atmosphere. 489 mg (6 mmol) of dimethylamine hydrochloride was added to the reaction solution, the temperature was raised from −40° C. to room temperature by detaching a cooling trough, and the resulting mixture was stirred for 2 hours after adding dimethylamine hydrochloride. 20 mL of pyridine solution of 7.03 g (30 mmol) of diphenyl phosphite was slowly dripped in at 20° C., and the mixture was stirred for 3 hours at room temperature under a nitrogen atmosphere. After adding 10 mL of triethylamine and 10 mL of water, the mixture was stirred for 1 hour at room temperature. The pyridine and dichloromethane were evaporated under reduced pressure, and 100 mL of water was added to the resulting residue for extraction, twice with 100 mL of chloroform. 4 mL of triethylamine and 100 mL of water to the organic layer were added to the organic layer for washing. The chloroform was evaporated under reduced pressure. The resultant was purified in a silica gel column by adding 0.5 mL of triethylamine to the crude product to obtain a white solid at 4.32 g (yield of 69%).

$^1$H NMR (400 MHz, CDCl$_3$), σ0.167 (6H, d, J=9.2 Hz), σ0.958 (9H, s), σ1.241 (9H, t, J=7.2 Hz), σ2.955 (6H, q,

J=7.2 Hz), σ3.963 (2H, s), σ4.544 (1H, s), σ4.97-5.02 (1H, m), σ5,411 (1H, t, J=5.6 Hz), σ5.713 (1H, d, J=8.0 Hz), 6.480 (1H, d, J=6.8 Hz), σ6.897 (1H, d, $J_{pH}$=628 Hz), σ7.416 (2H, t, J=7.2 Hz), σ7.551 (1H, t, J=7.2 Hz), σ8.005 (1H, d, J=8.0 Hz), σ8.058 (2H, d, J=8.0 Hz).

$^{31}$P NMR (162 MHz, CDCl$_3$), σ4.05

(4) Synthesis of Guanosine Monomer (4-1) Synthesis of N,N-dimethylformamidine Protected Guanosine

[Chemical formula 45]

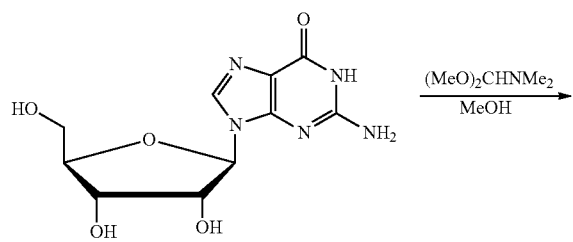

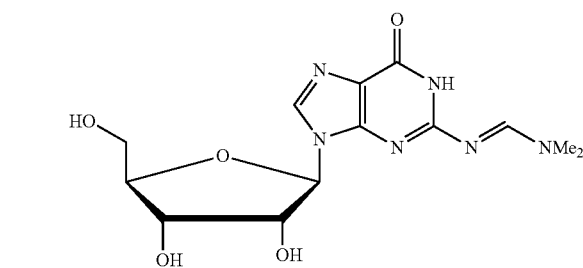

Under a nitrogen atmosphere, 5.66 g (20 mmol) of guanosine and 200 mL of methanol were placed in a three neck flask (300 mL) and stirred at room temperature. A mixture of 20 mL of dimethylformamide dimethyl acetal and 20 mL of methanol was added, and the mixture was stirred for 16 hours at room temperature under a nitrogen atmosphere. The produced solid was filtered, washed with methanol, and vacuum dried to obtain a white solid at 6.36 g (yield of 94%).

(4-2) Synthesis of 5'-t-butyldimethylsilyl·N,N-dimethylformamidine Protected Guanosine

[Chemical formula 46]

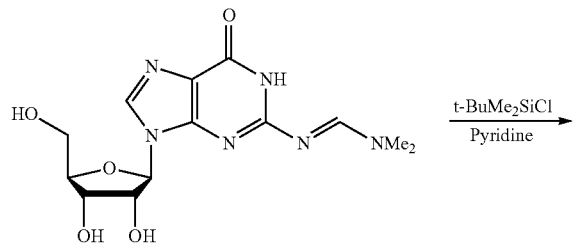

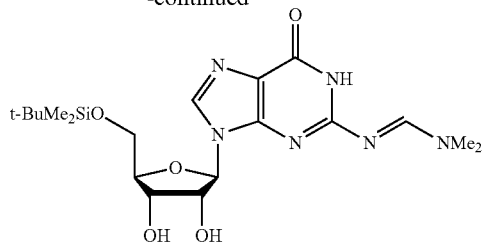

Under a nitrogen atmosphere, 3.38 g (10 mmol) of N,N-dimethylformamidine protected guanosine and 40 mL of dried pyridine were placed in a three neck flask (100 mL) and stirred at 0° C. 20 mL of dried pyridine solution of 2.26 g (15 mmol) of t-butylchlorodimethylsilane was slowly dripped in, and the mixture was stirred for 24 hours at room temperature under a nitrogen atmosphere. The pyridine was evaporated under reduced pressure, and 100 mL chloroform, 50 mL of methanol, and 100 mL of water were added to the resulting residue for extraction. The chloroform and methanol were evaporated under reduced pressure, and then the resultant was purified in a silica gel column to obtain a white solid at 4.11 g (yield of 91%).

(4-3) Synthesis of 5'-t-butyldimethylsilyl·N,N-dimethylformamidine protected-2-benzoyl guanosine-3'—H-phosphonate

[Chemical formula 47]

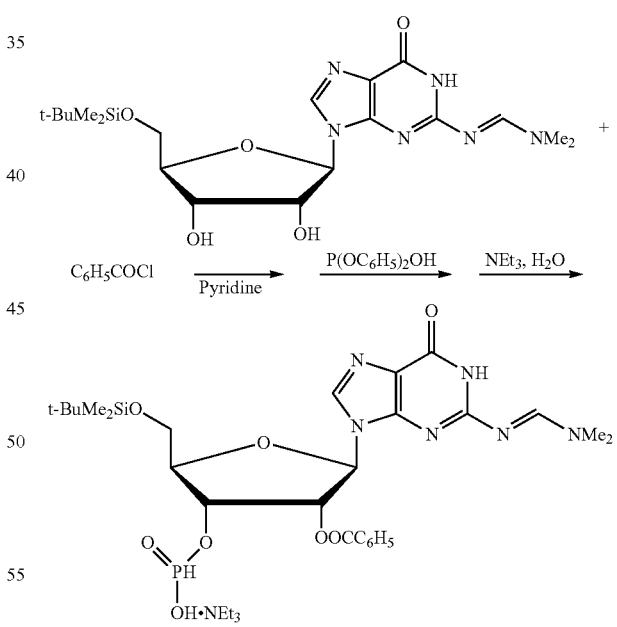

4.53 g (10 mmol) of protected guanosine and 60 mL of dried pyridine were placed in a three neck flask with a calcium chloride tube and stirred at −40° C. 20 mL of dried dichloromethane solution of 2.11 g (15 mmol) of benzoyl chloride was dripped in over 30 minutes, and the mixture was stirred for 30 minutes at −40° C. 20 mL of dried pyridine solution of 7.03 g (30 mmol) of diphenyl phosphite was dripped in over 15 minutes. After the dripping has been completed, a cooling trough was detached. The mixture was immersed in ice water and stirred for 1 hour at 0° C. 10 mL of triethylamine and 10 mL of water were added. The mixture was stirred at 0° C. and the reaction was stopped. The pyridine and dichloromethane were evaporated under reduced pressure, and water was added to the resulting residue for extraction, twice with chloroform. Triethylamine and water were added to the chloroform layer for washing and removing phosphorous acid and phenol. Chloroform was evaporated. The mixture was vacuum dried and triethylamine was removed as much as possible. The product of interest was then crudely purified in a silica gel column. Furthermore, 5 g of the resulting crude product was dissolved in a methanol/chloroform mixture solvent. The organic layer was washed with 5 wt. % of aqueous citric acid solution, and the byproducts in the chloroform layer were removed. After rewashing the aqueous layer with chloroform to remove byproducts, triethylamine was added to the aqueous layer so that the solution was alkaline, and the product of interest was extracted with chloroform. The chloroform was evaporated. The resultant was vacuum dried, and purified in a silica gel column after removing triethylamine as much as possible to obtain a white solid at 5.70 g (yield of 79%). $^1$H NMR (400 MHz, CDCl$_3$), σ0.121 (6H, d, J=4.8 Hz), σ0.938 (9H, s), σ1.234 (9H, t, J=7.2 Hz), σ2.964 (6H, q, J=7.2 Hz), σ3.077 (3H, s), σ3.233 (3H, s), σ3.482 (3H, s), 3.952 (2H, q, J=10.0 Hz), σ4.478 (1H, s), σ5.166 (1H, q, J=4.8 Hz), σ5.932 (1H, t, J=5.2 Hz), σ6.330 (1H, d, J=5.6 Hz), σ6.904 (1H, d, $J_{pH}$=624 Hz), σ7.392 (2H, t, J=7.6 Hz), σ7.539 (1H, t, J=7.6 Hz), σ7.959 (1H, s), σ8.040 (2H, d, J=7.2 Hz), σ8.725 (1H, br), σ8.763 (1H, s). $^{31}$P NMR (162 MHz, CDCl$_3$), σ3.51

(Example 2) Synthesis of RNA Oligomer

The monomer synthesized above was used to synthesize an RNA oligomer by liquid phase synthesis.

TABLE 2

| Reaction condition | |
| --- | --- |
| Reaction solvent | Pyridine: MeCN = 1:1 (0.05M) |
| Reaction temperature | 25° C. |
| Starting base | 5'-OH-dT-3'-O-suc-O-PEG (1 eq.) |
| Monomer | TBDMS-rU-H-phosphonate (1.3 eq.) |
| Condensing agent | Pivaloyl chloride (6.5 eq.) |
| Oxidizing agent | 0.1M I$_2$ (1.5 eq.) |
| Desilylation agent | 1M TBAF (15 eq.) |

An elongation reaction was performed under the above reaction conditions. Purification was performed by ether precipitation upon each elongation.

TABLE 3

Results of synthesis upon 20 base elongation

| Number of bases | Sequence (5'-HO-R-3'-O-suc-O-PEG) | Mean molecular weight (PEGylation) | Yield mg | Yield μmol | LC purity (%) after precipitation |
| --- | --- | --- | --- | --- | --- |
| 1 | dT | 5342 | 533.8 | 99.9 | — |
| 2 | rUdT | 5753 | 547.1 | 95.1 | 93.1 |
| 5 | rU$_4$dT | 6983 | 345.6 | 49.5 | 86.2 |
| 9 | rU$_8$dT | 8624 | 217.0 | 25.2 | 75.4 |
| 10 | rU$_9$dT | 9034 | 214.4 | 23.7 | 70.6 |
| 15 | rU$_{14}$dT | 11086 | 173.7 | 15.7 | 60.0 |
| 19 | rU$_{18}$dT | 12727 | 133.8 | 10.5 | 59.2 |
| 20 | rU$_{19}$dT | After deprotection 6059.38 | After HPLC purification 14.1 μg | After HPLC purification 2.3 nmol | Yield 0.002% |

Characterization

After obtaining 5'-TBDMS-rU$_{19}$dT-3'—O-suc-O-PEG elongated to the 20th base, the benzoyl group at position 2' was protected and 3'-suc-O-PEG was deprotected with ethylenediamine and then subjected to HPLC purification to obtain 5'-TBDMS-rU$_{19}$dT-3'—OH. Further, the TBDMS group at position 5' was deprotected with TBAF, and a sample subjected again to HPLC purification was analyzed by LC-MS to confirm m/z=6058.9 (theoretical value: 6059.38), which matched the molecular weight of 5'—HO-rU$_{19}$dT-3'—OH (see FIG. 1).

Elongation reaction for introducing various bases

TABLE 4

| Conditions for 10 base elongation reaction | |
| --- | --- |
| Reaction condition | |
| Reaction solvent | Pyridine: MeCN = 1:1 (0.05M) |
| Reaction temperature | 25° C. |
| Starting base | 5'-OH-dT-3'-O-suc-O-PEG (1 eq.) |
| Monomer | TBDMS-rU-H-phosphonate (1.3 eq.) |
| Condensing agent | Pivaloyl chloride (6.5 eq.) |
| Oxidizing agent | 0.1M I$_2$ (1.5 eq.) |
| Desilylation agent | 1M TBAF (15 eq.) |

The results of elongation up to 10 bases while introducing various base types are shown below.

TABLE 5

Results of synthesis from 10 base elongation reaction

| Number of bases | Sequence (5'-HO-R-3'-O-suc-O-PEG) | Mean molecular weight (PEGylation) | Yield mg | Yield μmol | LC purity (%) after precipitation |
| --- | --- | --- | --- | --- | --- |
| 1 | dT | 5342 | 606.1 | 113.5 | |
| 2 | rUdT | 5753 | 620.7 | 107.9 | 94.9 |
| 3 | rU$_2$dT | 6163 | 583.9 | 94.7 | 94.4 |
| 4 | rU$_3$dT | 6573 | 590.2 | 89.8 | 91.6 |
| 5 | rArU$_3$dT | 7006 | 614.8 | 87.8 | 88.6 |
| 6 | rGrArU$_3$dT | 7526 | 616.6 | 81.9 | 87.0 |
| 7 | rCrGrArU$_3$dT | 7936 | 541.2 | 68.2 | 84.1 |

TABLE 5-continued

Results of synthesis from 10 base elongation reaction

| Number of bases | Sequence (5'-HO-R-3'-O-suc-O-PEG) | Mean molecular weight (PEGylation) | Yield mg | Yield μmol | LC purity (%) after precipitation |
|---|---|---|---|---|---|
| 8 | rUrCrGrArU$_3$dT | 8346 | 519.0 | 62.2 | 86.6 |
| 9 | rU$_2$rCrGrArU$_3$dT | 8756 | 542.1 | 61.9 | 84.2 |
| 10 | rU$_3$rCrGrArU$_3$dT | After deprotection 3058.82 | After HPLC purification 267.1 μg | After HPLC purification 87.3 nmol | Yield 0.077% |

Figure 2:
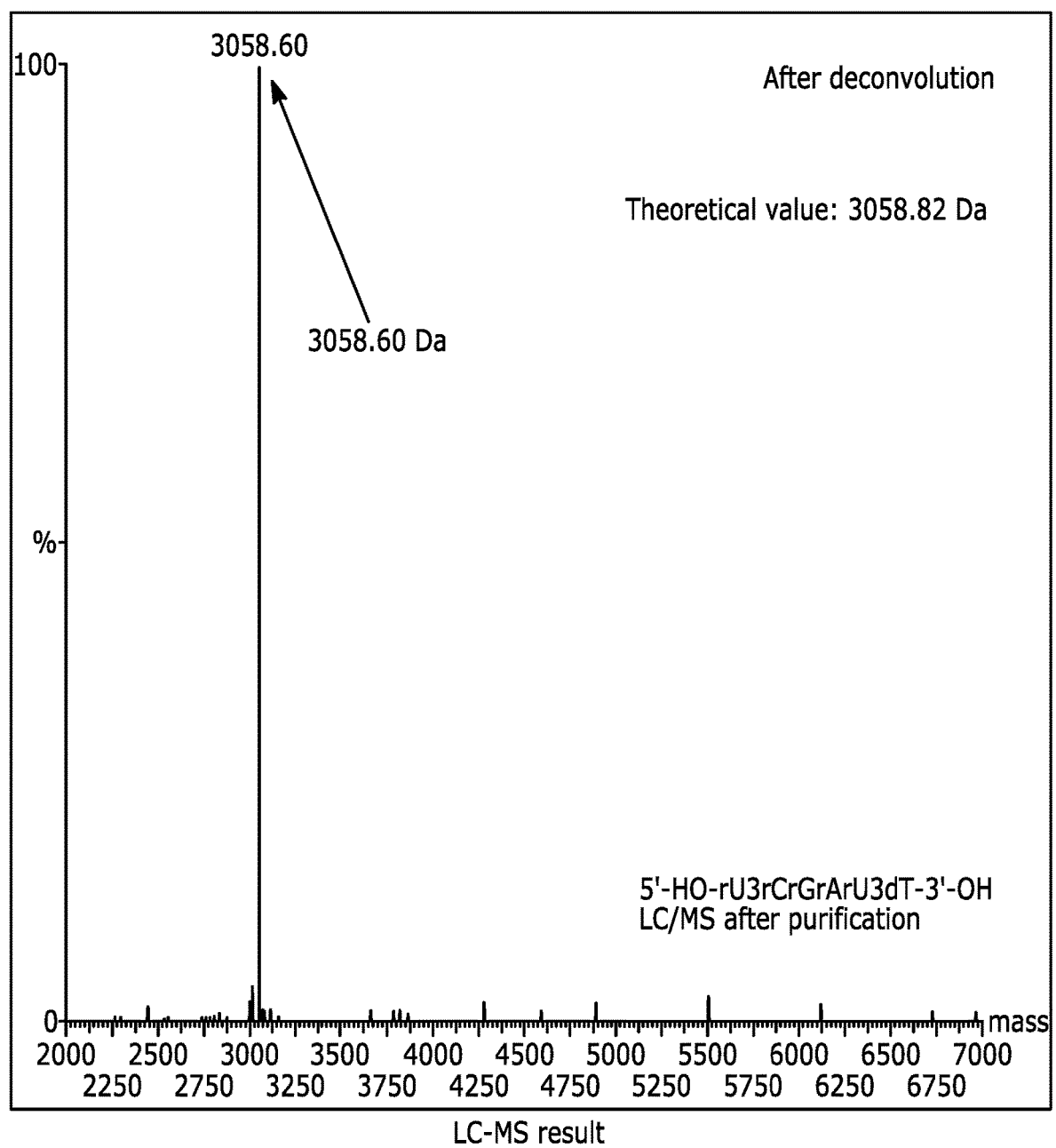
FIG. 2 shows a result of LC-MS analysis on 5'—HO-rU$_3$rCrGrArU$_3$dT-3'—OH.

In the same manner as the elongation to up to 20 bases, 5'-TBDMS-rU$_3$rCrGrArU$_3$dT-3'—O-suc-O-PEG was obtained, and then the benzoyl group at position 2' was protected and 3'-suc-O-PEG was deprotected with ethylenediamine. HPLC purification was performed to obtain 5'-TBDMS-rU$_3$rCrGrArU$_3$dT-3'—OH. Further, the TBDMS group at position 5' was deprotected with TBAF, and a sample subjected again to HPLC purification was analyzed by LC-MS to confirm m/z=3058.60 (theoretical value: 3058.82), which matched the molecular weight of 5'—HO-rU$_3$rCrGrArU$_3$dT-3'—OH (see FIG. 2).

As described above, the present invention is exemplified by the use of its preferred embodiments. However, it is understood that the scope of the present invention should be interpreted based solely on the Claims. It is also understood that any patent, patent application, and reference cited herein should be incorporated herein by reference in the same manner as if the contents are specifically described herein.

INDUSTRIAL APPLICABILITY

The present invention is useful in the drug development industry and reagent industry using nucleic acid medicaments and the like.

Sequence Listing Free Text

SEQ ID NO: 1: Sequence with 10 bases in Table 3
SEQ ID NO: 2: Sequence with 15 bases in Table 3
SEQ ID NO: 3: Sequence with 19 bases in Table 3
SEQ ID NO: 4: Sequence with 20 bases in Table 3
SEQ ID NO: 5: Sequence with 10 bases in Table 5

The invention claimed is:

1. A method of manufacturing a compound represented by chemical formula 1:

[Chemical formula 1]

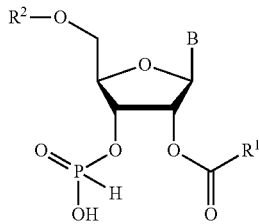

wherein $R^1$ represents a group selected from the group consisting of a substituted or unsubstituted aryl group and a substituted or unsubstituted heteroaryl group, $R^2$ represents a protecting group of a hydroxy group or a hydrogen atom, and B represents a nucleic acid base that may or may not have a protecting group, or a salt thereof, or solvate thereof, wherein the method comprises:

(1) reacting a compound of chemical formula 2 with a compound of chemical formula 3 to obtain a compound of chemical formula 4:

[Chemical formula 2]

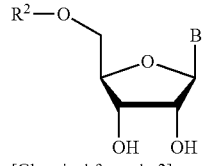

[Chemical formula 3]

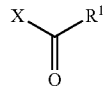

wherein X is a halogen atom,

[Chemical formula 4]

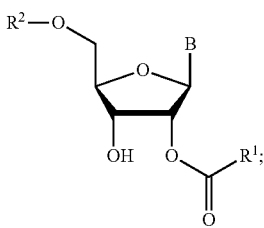

and (2) reacting the compound of chemical formula 4 with P(OR$^3$)(OR$^{3'}$)OH to obtain the compound of chemical formula 1;
wherein R$^3$ and R$^{3'}$ each independently represent a group selected from the group consisting of a substituted or unsubstituted aryl group and a substituted or unsubstituted heteroaryl group,
wherein step 1 and step 2 are performed in a single reaction vessel.

2. The method of claim 1, wherein the nucleic acid base is selected from the group consisting of

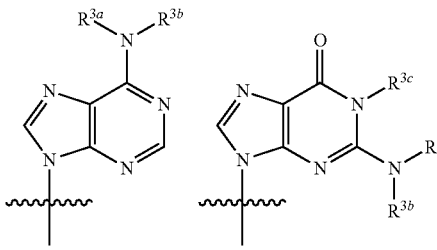

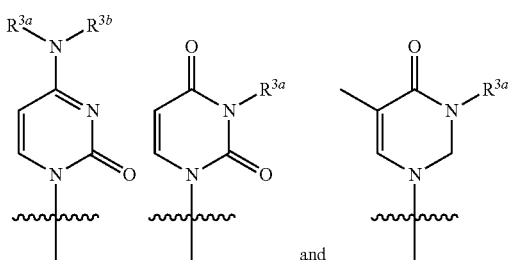

and wherein R$^{3a}$, R$^{3b}$, and R$^{3c}$ each independently represent a group selected from the group consisting of a hydrogen atom, a substituted or unsubstituted straight or branched alkylacyl group, a substituted or unsubstituted arylacyl group, a substituted or unsubstituted alkyl group, a substituted or unsubstituted cycloalkyl group, a substituted or unsubstituted aryl group, and a substituted or unsubstituted heteroaryl group, or R$^{3a}$ and R$^{3b}$ are groups together forming an amidine protecting group.

3. The method of claim 2, wherein the amidine protecting group is an N,N-dimethylformamidino group or an N,N-dimethylacetamidino group.

4. The method of claim 1, wherein R$^1$ is a substituted or unsubstituted aryl group.

5. The method of claim 4, wherein the substituted or unsubstituted aryl group is a phenyl group.

6. The method of claim 1, wherein the protecting group of a hydroxy group is selected from the group consisting of an ether based protecting group, a silyl ether based protecting group, an acetal based protecting group, and an acyl based protecting group.

7. The method of claim 6, wherein the ether based protecting group is

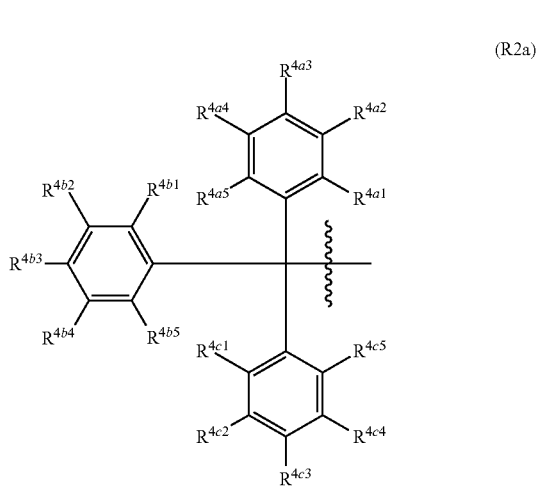

wherein R$^{4a1}$, R$^{4a2}$, R$^{4a3}$, R$^{4a4}$, R$^{4a5}$, R$^{4b1}$, R$^{4b2}$, R$^{4b3}$, R$^{4b4}$, R$^{4b5}$, R$^{4c1}$, R$^{4c2}$, R$^{4c3}$, R$^{4c4}$, and R$^{4c5}$ are each independently a group selected from the group consisting of a hydrogen atom, a substituted or unsubstituted straight or branched alkoxy group, and a substituted or unsubstituted straight or branched alkyl group.

8. The method of claim 7, wherein the substituted or unsubstituted straight or branched alkoxy group is a straight or branched perfluoroalkoxy group.

9. The method of claim 7, wherein the substituted or unsubstituted straight or branched alkyl group is a straight or branched perfluoroalkyl group.

10. The method of claim 6, wherein the silyl ether based protecting group is

wherein R$^{4d}$, R$^{4e}$, and R$^{4f}$ are each independently a group selected from the group consisting of a substituted or unsubstituted straight or branched alkyl group, a substituted or unsubstituted aryl group, and a substituted or unsubstituted alkenyl group.

11. The method of claim 10, wherein the substituted or unsubstituted alkenyl group is an allyl group.

12. The method of claim 6, wherein the silyl ether based protecting group is

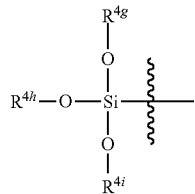
(R2c)

wherein $R^{4g}$, $R^{4h}$ and $R^{4i}$ are each independently a group selected from the group consisting of a substituted or unsubstituted hydrocarbon group, a substituted or unsubstituted silyl group, and a substituted or unsubstituted silyloxyalkyl group.

13. The method of claim 12, wherein the silyl group is substituted with 1 to 3 alkyl groups.

14. The method of claim 12, wherein the substituted or unsubstituted hydrocarbon group is selected from the group consisting of a substituted or unsubstituted straight or branched alkyl group, a substituted or unsubstituted straight or branched alkenyl group, a substituted or unsubstituted straight or branched alkynyl group, a substituted or unsubstituted cycloalkyl group, a substituted or unsubstituted cycloalkenyl group, a substituted or unsubstituted aryl group, and a substituted or unsubstituted straight or branched arylalkyl group.

15. The method of claim 14, wherein the substituted or unsubstituted straight or branched alkyl group is a straight or branched haloalkyl group.

16. The method of claim 15, wherein the straight or branched haloalkyl group is a straight or branched perfluoroalkyl group.

17. A kit for manufacturing a compound of chemical formula 1:

[Chemical formula 1]

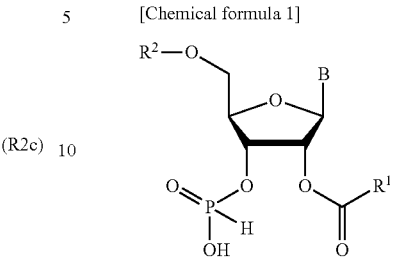

comprising:
(1) a compound of chemical formula 11:

[Chemical formula 11]

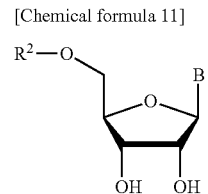

wherein $R^2$ represents a protecting group of a hydroxy group or a hydrogen atom, and B represents a nucleic acid base that may or may not have a protecting group;

(2) a compound of chemical formula 12:

[Chemical formula 12]

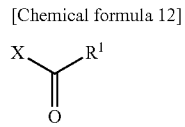

wherein $R^1$ represents a group selected from the group consisting of a substituted or unsubstituted aryl group and a substituted or unsubstituted heteroaryl group, and X is a halogen atom; and (3) $P(OR^3)(OR^{3'})OH$
wherein $R^3$ and $R^{3'}$ each independently represent a group selected from the group consisting of a substituted or unsubstituted aryl group and a substituted or unsubstituted heteroaryl group.

\* \* \* \* \*

```
SEQUENCE LISTING

<160> NUMBER OF SEQ ID NOS: 5

<210> SEQ ID NO 1
<211> LENGTH: 10
<212> TYPE: DNA
<213> ORGANISM: artificial sequence
<220> FEATURE:
<223> OTHER INFORMATION: combined DNA/RNA molecule
<220> FEATURE:
<221> NAME/KEY: RNA
<222> LOCATION: (1)..(9)
<220> FEATURE:
<221> NAME/KEY: DNA
<222> LOCATION: (10)..(10)

<400> SEQUENCE: 1
uuuuuuuuut                                                          10

<210> SEQ ID NO 2
<211> LENGTH: 15
<212> TYPE: DNA
<213> ORGANISM: artificial sequence
<220> FEATURE:
<223> OTHER INFORMATION: combined DNA/RNA molecule
<220> FEATURE:
<221> NAME/KEY: RNA
<222> LOCATION: (1)..(14)
<220> FEATURE:
<221> NAME/KEY: DNA
<222> LOCATION: (15)..(15)

<400> SEQUENCE: 2
uuuuuuuuuu uuuut                                                    15

<210> SEQ ID NO 3
<211> LENGTH: 19
<212> TYPE: DNA
<213> ORGANISM: artificial sequence
<220> FEATURE:
<223> OTHER INFORMATION: combined DNA/RNA molecule
<220> FEATURE:
<221> NAME/KEY: RNA
```

```
<222> LOCATION: (1)..(18)
<220> FEATURE:
<221> NAME/KEY: DNA
<222> LOCATION: (19)..(19)

<400> SEQUENCE: 3
uuuuuuuuuu uuuuuuuut                                              19

<210> SEQ ID NO 4
<211> LENGTH: 20
<212> TYPE: DNA
<213> ORGANISM: artificial sequence
<220> FEATURE:
<223> OTHER INFORMATION: combined DNA/RNA molecule
<220> FEATURE:
<221> NAME/KEY: RNA
<222> LOCATION: (1)..(19)
<220> FEATURE:
<221> NAME/KEY: DNA
<222> LOCATION: (20)..(20)

<400> SEQUENCE: 4
uuuuuuuuuu uuuuuuuut                                              20

<210> SEQ ID NO 5
<211> LENGTH: 10
<212> TYPE: DNA
<213> ORGANISM: artificial sequence
<220> FEATURE:
<223> OTHER INFORMATION: combined DNA/RNA molecule
<220> FEATURE:
<221> NAME/KEY: RNA
<222> LOCATION: (1)..(9)
<220> FEATURE:
<221> NAME/KEY: DNA
<222> LOCATION: (10)..(10)

<400> SEQUENCE: 5
uuucgauuut                                                        10
```